US005670309A

United States Patent [19]

Norrby et al.

[11] Patent Number: 5,670,309

[45] Date of Patent: Sep. 23, 1997

[54] METHODS AND DIAGNOSTIC KITS FOR THE DETECTIONS OF HIV-2-SPECIFIC ANTIBODIES EMPLOYING POLYPEPTIDES OBTAINED FROM THE SIMIAN IMMUNODEFICIENCY VIRUS

[75] Inventors: Erling C. J. Norrby, Lidingo, Sweden; D. Elliot Parks, Del Mar; Richard A. Lerner, La Jolla, both of Calif.

[73] Assignee: Johnson & Johnson, New Brunswick, N.J.

[21] Appl. No.: 192,782

[22] Filed: Feb. 7, 1994

Related U.S. Application Data

[63] Continuation of Ser. No. 61,274, May 13, 1993, abandoned, which is a continuation of Ser. No. 782,742, Oct. 17, 1991, abandoned, which is a continuation of Ser. No. 597,096, Oct. 15, 1990, abandoned, which is a continuation of Ser. No. 83,682, Aug. 7, 1987, abandoned.

[30] Foreign Application Priority Data

Apr. 16, 1987 [SE] Sweden ................................ 87016283

[51] Int. Cl.$^6$ ............................ G01N 33/53; C12Q 1/70; A61K 39/21

[52] U.S. Cl. ............................ 435/5; 435/7.1; 424/188.1; 424/208.1

[58] Field of Search ...................... 435/5, 7.1, 7.92–7.95, 435/974; 530/350, 324–329, 812, 826

[56] References Cited

U.S. PATENT DOCUMENTS

| | | |
|---|---|---|
| 4,629,783 | 12/1986 | Cosand . |
| 4,631,211 | 12/1986 | Houghten . |
| 4,735,896 | 4/1988 | Wang et al. . |
| 4,839,288 | 6/1989 | Montagnier et al. . |
| 5,156,949 | 10/1992 | Luciw et al. ................................ 435/5 |

FOREIGN PATENT DOCUMENTS

| | | |
|---|---|---|
| 0 199 438 | 10/1986 | European Pat. Off. . |
| 0 201 716 | 11/1986 | European Pat. Off. . |
| 0 220 273 | 11/1986 | European Pat. Off. . |
| 0 214709 | 3/1987 | European Pat. Off. . |
| 0 284 383 | 9/1988 | European Pat. Off. . |
| 0 283 327 | 10/1988 | European Pat. Off. . |
| 0 292 454 | 11/1988 | European Pat. Off. . |
| 2614025 | 10/1988 | France . |
| WO 88/05440 | 7/1988 | WIPO . |

OTHER PUBLICATIONS

U.S. Ser. No. 35,408, Cosand et al., filed Apr. 07, 1987.

Barnes, D.M. *Science*, 235(4789):634(1987).

Benjamin et al., *Ann. Rev. Immunol.*, 2:67–101 (1984).

Biberfeld et al., *Aids Research and Human Retroviruses*, 3(3):241–143 (1987).

Cabradilla, et al., *Bio/Technology*, 4:128–133 (1986).

Chakrabarti et al., *Nature*, 328:543–547 (1987).

Chang, et al., *Bio/Technology*, 3:905–908 (1985).

Clavel et al., *Science*, 233:343–346 (1986).

Clavel et al., *Nature*, 324:691–695 (1986).

DiMarzo Veronese, F., et al., *Science*, 229:1402–1405 (1985).

Gnann, et al., *J. Infectious Diseases*, 156(2):261–267 Aug. 1987.

Gnann, et al., *J. Virology*, 61:2639–2641 (Aug. 1987).

Green et al., *Cell*, 28:447–487 (1982).

Guyader et al., *Nature*, 326: 662–669 Apr. 16, 1987.

Hirsch, et al., *Cell*, 49:307–319 May 8, 1987.

Kanki, et al., *Science*, 228:1199–1201 (1985).

Kanki et al., *Science*, 232:238–243 (1986).

Kornfeld, et al., *Nature*, 326:610–613 (1987).

Kornfeld, et al., *Nature*, 326:548 (1987).

Sutcliffe et al., *Science*, 219:660–666 (1984).

Wang et al., *Proc. Nat'l Acad. Sci., USA*, 83:1659–6163 (Aug. 1986).

Houghten, *Proc. Natl. Acad. Sci., U.S.A.*, 82:5131–5135 (1985).

Wang et al, "Detection of Antibodies to Human T-Lymphotropic Virus Type III by Using a Synthetic Peptide of 21 Amino Acid Residues Corresponding to a Highly Antigenic segment of gp41 Envelope Protein" Proc. Natl. Acad Sci. USA 83(1986) Jun. 1959–Jun. 1963.

Chakrabarti et al, "Sequence of Simian Immunodeficiency Muss From Macaque and its Relationship to Other Human and Simian Retroviruses," Nature 326(1987)543–550.

Geysen et al., J. Molec. Recog. 1:33–41, 1988.

Getzoff et al., Adv. Immunol. 43:1–98, 1988.

Gnann et al., Science 237:1346–1349, 1987.

Starcich et al., Cell 45:637–648, 1986.

Wilson et al., Proc. Natl. Acad. Sci. USA 82:5255–5259, 1985.

Mateu et al., Proc. Natl. Acad. Sci. USA 86:5883–5887, 1989.

Sutcliffe et al., *Science*, 219:660–666 (1993).

*Primary Examiner*—Christine M. Nucker

*Assistant Examiner*—Jeffrey S. Parkin

*Attorney, Agent, or Firm*—Welsh & Katz, Ltd.

[57] ABSTRACT

The simian immunodeficiency virus (SIV) is genotypically and phenotypically similar to the human immunodeficiency virus type 2 (HIV-2). Both viruses display similar structural, biological, and immunological properties. The external envelope glycoprotein (EMP) and transmembrane envelope glycoprotein (TMP) appear to be formed from the cleavage of a precursor glycoprotein. Despite these similarities, a number of differences exist as evidenced by the different migratory properties of the envelope glycoproteins. The present invention discloses novel SIV peptides, obtained from the transmembrane envelope glycoprotein, that display immunological cross-reactivity with HIV-2-specific antisera. Epitope mapping studies revealed that the amino acid sequence —CAFRQVC—, which corresponds to amino acid residues 614–620, is a sine qua non for the retention of this immunological cross-reactivity. These peptides are useful in diagnostic methods for the detection of HIV-2-specific antibodies in infected patients.

15 Claims, 3 Drawing Sheets

FIG. 1

STLV-III SEQUENCE:

5 10 15 20 25 30

AIEKYLEDQAQLNAWGCAFRQVCHTTVPWPNAS

FIG. 2

HIV-1 SEQUENCE:

5 10 15 20 25 30

AVERYLKDQQLLGIWGCSGKLICTTAVPWNAS

POLYPEPTIDES III/IV
(V-I-SPECIFIC)
ELISA

METHODS AND DIAGNOSTIC KITS FOR THE DETECTIONS OF HIV-2-SPECIFIC ANTIBODIES EMPLOYING POLYPEPTIDES OBTAINED FROM THE SIMIAN IMMUNODEFICIENCY VIRUS

This application is a continuation of Ser. No. 08/061,274, filed May 13, 1993, now abandoned, which is a continuation of Ser. No. 07/782,742, filed Oct. 17, 1991, now abandoned, which is a continuation of Ser. No. 07/597,096, filed Oct. 15, 1990, now abandoned, which is a continuation of Ser. No. 07/083,682, filed Aug. 07, 1987, now abandoned.

TECHNICAL FIELD

The present invention contemplates a novel polypeptide antigen related to the simian virus STLV-III and to its use in diagnostic systems and assay methods.

BACKGROUND OF THE INVENTION

The acquired immune deficiency syndrome (AIDS) has now spread worldwide and appears to be an acute public health problem, particularly in Africa. A retrovirus designated human immunodeficiency virus type 1 (HIV-1), but previously known as LAV, HTLV-III or ARV, was shown to cause AIDS in the different areas afflicted by the epidemics, including North America, Western Europe and Central Africa.

Studies of HIV-1 at the molecular level have revealed some differences in the nucleotide sequence of North-American and African isolates. This sequence variation is also present, though to a lesser extent, among different isolates from the USA. However, the North American, Western European and Central African isolates appear to have similar biological properties and antigenically cross-reactive proteins with the same relative molecular mass.

Individuals infected with HIV-1 develop antibodies to the gag-gene encoded viral core proteins designated p19, p24, and to their precursor protein designated p55. In addition, antibodies against env-gene encoded envelope glycoproteins gp120 (the extracellular glycoprotein or EGP), gp41 (the transmembrane protein or TMP) and their precursor glycoprotein designated gp160 are also observed.

A large number of AIDS patients show a disappearance of antibodies to the HIV-1 core proteins at an advanced state of the disease, but retain antibodies immunoreactive with the envelope antigens. The envelope products are regularly detected by antibodies in sera from patients at different stages of HIV-1 infection. Although few reports are available on seroconversion to HIV-1, the emergence of antibodies to the envelope proteins seems to shortly precede emergence of antibodies to the core proteins. See Carlson et al., *Lancet*, i:361–362, (1987). For these reasons, the use of antigens representing the env-gene products have significant importance in diagnosis of exposure to AIDS related retroviruses.

Because AIDS can be transmitted by blood products, there has, from the initial recognition of the disease, been a strong impetus to develop diagnostic tests to screen blood for antibodies or antigens specific for the infecting virus. Efforts in this area have borne fruit, and by the end of 1985 five companies had been approved to market tests to detect antibodies to HIV-1 virus. These tests all rely for detection of those antibodies on the use of viral proteins obtained from cultured HIV-infected T-lymphocytes. The virus obtained from the cultured cells is disrupted (e.g., with detergent) and a fluid (called "viral lysate") is obtained. This lysate (containing a variety of fragments of viral and cellular protein) is then typically used as the solid phase component of an immunoassay.

While the existing tests appear to have significantly diminished the transmission of HIV-1 via blood products, the viral lysate based tests have some significant disadvantages, including results that indicate a high rate of false positives. The false positives are thought to be due in part to the presence of non-viral proteins in the viral lysate preparations used in the solid phase component of the current assays.

In an attempt to reduce the rate of false positive results, the art has begun to develop site-directed serological assays employing synthetic polypeptides that mimic naturally occurring antigenic determinants on viral proteins. For instance, the U.S. Pat. No. 4,629,783 to Cosand, Wang et al., *Proc. Natl. Acad. Sci. USA*, 83:6159–6163 (1986), and Kennedy et al., *Science*, 231:1556–1559 (1986) describe several polypeptides said to be capable of mimicking antigenic determinants formed by various HIV-1 proteins, including the TMP (gp41). U.S. patent applications No. 843,437, filed Mar. 24, 1986, and No. 25,108, filed Mar. 30, 1987, both assigned to Johnsonn & Johnaon, Inc., New Brunswick, N.J., also describe HIV-1 TMP-related polypeptides. Disclosures similar to those contained in the first application identified above were made by Rosen et al. at the Second International Conference on AIDS in Paris, France in June, 1986.

Another significant disadvantage of the current methods for diagnosing exposure to AIDS-related viruses is that they rely on the use of HIV-1 derived antigens and thus give false negative results for individuals exposed to the antigenically distinct West African AIDS-related retroviruses, designated herein as HIV type 2 (HIV-2). More than 20 HIV-2 isolates have been made from patients with AIDS and related conditions, mainly from West Africans, but also from some Europeans. Thus, an assay specific for HIV-2 is needed for screening donated blood and for diagnosis of HIV-2 infection. Bruin-Vezinet, *Lancet*, i:128–132 (1987).

HIV-2 is structurally, biologically and antigenically related to HIV-1 and the simian T-lymphotrophic virus type III isolated from macaques (STLV-$III_{mac}$), a virus causing an AIDS-like disease in its simian host. All three viruses appear to contain EMP and TMP proteins that are formed by cleaveage of a precursor protein. However, the apparent molecular weight of each of these proteins varies between HIV-1, HIV-2 and STLV-III and is thus one feature that can be used to distinguish among these viruses. For instance, the apparent molecular weight, in kilodaltons, of the TMPs of HIV-1, HIV-2 and STLV-$III_{mac}$ are 41, 36, and 32, respectively.

Each of HIV-1, HIV-2 and STLV-$III_{mac}$ also exhibit cytopathogenicity and tropism for cells carrying the CD4 (T4) antigen (T4 lymphocytes). In addition, all three viruses have antigenically cross-reactive core proteins. Daniel et al., *Science*, 228:1201–04 (1985); Bruin-Vezinet et al., supra. However, while the envelope proteins, including the TMPs, of HIV-2 and STLV-$III_{mac}$ are antigenically cross-reactive, neither appears to share antigenic determinants with the HIV-1 TMP. Clavel et al., *Science*, 233:343–346 (1986).

While the DNA sequence of the env-gene of STLV-$III_{mac}$ has not been reported, Guyader et al., *Nature*, 326:662–669 (1987) have reported both the DNA sequence and the deduced amino acid residue sequence of the HIV-2 env-gene protein products. In comparing the EGP proteins of HIV-1 and HIV-2, Guyader et al. found them to be "very distantly related" because there was only 44.8% homology in their amino acid residue sequences. Similarly, the amino acid residue sequences of the HIV-1 and HIV-2 TMP proteins were only 44.8% homologous. However, even to obtain these levels of homology, Guyader et al. had to put large insertions into the amino acid residue sequences, particularly when aligning the EGPs where only short, widely separated domains are conserved between HIV-1 and HIV-2.

Guyader et al. also reported that 22 of 23 cysteine residues found in the HIV-1 envelope proteins could be aligned with cysteine residues found in the corresponding HIV-2 proteins. However, the HIV-2 proteins were found to contain an additional seven cysteine residues that were found mostly in regions representing insertions relative to HIV-1. Thus, it was concluded that "the folding of the HIV-2 EGP could be different from that of HIV-1, and some regions, therefore, might be exposed in a different manner." No reason was set forth indicating a similar conclusion was not applicable to the TMP proteins of HIV-1 and HIV-2.

Hirsch et al., *Cell*, 49:307–319 (1987) report the nucleotide sequence of the genome of a STLV-III virus isolated from African green monkeys (STLV-$III_{agm}$). According to Hirsch et al., the STLV-$III_{agm}$ TMP is 140 amino acids shorter than that of HIV-1 and appears to contain fewer potential glycosylation sites. At the same time, Hirsch et al. describe the STLV-$III_{agm}$ and HIV-1 TMPs as being relatively well connserved, 49% of the amino acids being the same and 32% representing conservative substitutions.

Finally, according to Hirsch et al., the STLV-$III_{agm}$ isolate they examined was virtually identical, by DNA hybridization, to one STLV-$III_{agm}$ isolate but readily distinguishable by restriction site mapping from a second STLV-$III_{mac}$ isolate. Thus, the relationship of STLV-$III_{mac}$ to STLV-$III_{agm}$ and HIV-1 is, at present, not well defined.

BRIEF SUMMARY OF THE INVENTION

The present invention provides site-directed serological reagents, assay methods and diagnostic kits useful for diagnosing exposure to AIDS-related West African retroviruses (HIV-2 and STLV-III retroviruses). That is, the present invention provides an STLV-III-related polypeptide that immunologically cross-reacts with antibodies induced by HIV-2 infections in humans.

Thus, the present invention contemplates a STLV-III-related polypeptide defined as consisting essentially of a polypeptide that 1) includes an amino acid residue sequence represented by the formula:

—CAFRQVC—, 2) contains no more than about 50 amino acid residues, and 3) has the ability to immunoreact with antibodies induced by a HIV-2 retrovirus. Preferably, a STLV-III-related polypeptide contains no more than 33 amino acid residues and has a sequence homologous to a portion of the sequence shown in FIG. 1.

Also contemplated is a method of assaying for the presence of anti-HIV-2 antibodies in a body fluid sample. The method comprises forming an immunoreaction admixture by admixing the sample to be assayed with a STLV-III-related polypeptide of the present invention. The admixture is maintained for a time period sufficient for any anti-HIV-2 antibodies present in the sample to immunoreact with the STLV-III-related polypeptide antigen to form a polypeptide-containing immunoreaction product. Assaying for the presence of any polypeptide-containing immunoreaction product formed thereby provides a measure of the presence of anti-HIV-2 antibodies in the sample.

Further contemplated by the present invention is a diagnostic system in kit form useful for performing the contemplated assay methods. The system comprises a package that includes a STLV-III-related polypeptide of the present invention present in an amount sufficient to carry out at least one assay.

Preferably, the diagnostic system further includes either a HIV-1-related di-cys polypeptide or a HIV-1-related di-leu polypeptide, or both in an amount sufficient to perform at least one assay for the presence of antibodies to HIV-1. More preferably, HIV-1-related di-cys and di-leu polypeptide are both included in the kit admixed with each other. In another preferred embodiment, a STLV-III-related, HIV-1-related di-cys and HIV-1-related di-leu polypeptide are included in the kit admixed with each other. Most preferred are kits wherein included STLV-III-related and HIV-1-related polypeptides, either separately or in admixture, are operatively affixed to a solid matrix, thereby forming a solid support.

Thus, the present invention provides several benefits and advantages. One benefit provided by the diagnostic systems and methods of this invention is the ability to screen a body fluid such as a blood product for exposure to both of the currently known types of AIDS-related viruses. In addition, because the present invention provides immunological site-specific diagnostic reagents, exposure to HIV-1 versus HIV-2 can be advantageously distinguished.

A further advantage provided by the present invention is that production and use of the contemplated system and methods for diagnosing exposure to both the HIV-1 and HIV-2 AIDS causing viruses can now be performed without the necessity or difficulty of producing potentially infectious genetic material as is the case where a viral lysate is used as antigen.

BRIEF DESCRIPTION OF THE DRAWINGS

In the Figures forming a portion of the disclosure of this invention:

FIG. 1 illustrates a portion of the STLV-$III_{mac}$ TMP amino acid residue sequence. The sequence is shown from left to right and in the direction of amino-terminus to carboxy-terminus in a single-letter code. The residue positions have been numbered as illustrated from 1–33.

FIG. 2 illustrates, in a manner similar to FIG. 1, a portion of the amino acid residue sequence of the HIV-1 TMP and represent gp41 amino acid residues 589–610 as described in Ratner et al., *Nature*, 313:277–283 (1985). However, for ease of discussion, those residue positions have been renumbered as illustrated from 1–32.

Figure 3A:
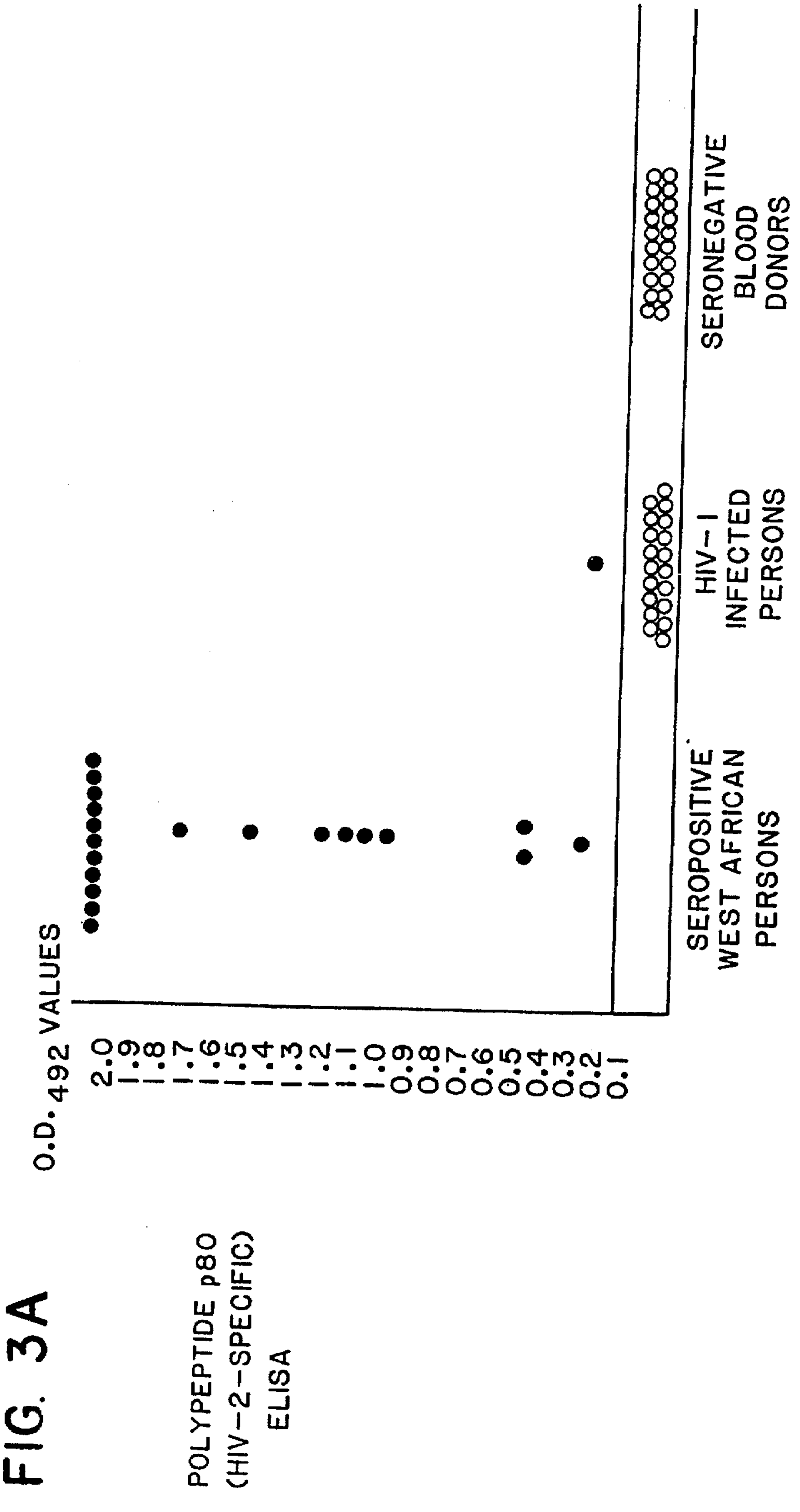
FIG. 3 contains 2 panels illustrating antibody determinations using a diagnostic system of this invention to assay (a) 20 sera from individuals in Guinea-Bissau previously determined to have antibodies against HIV-related viruses (West Africans), (b) 20 sera from HIV-1-infected individuals and (c) 20 sera from blood donors without antibodies to HIV-1 or HIV-2. Sera were considered positive (closed symbols) when they produced optical density (O.D.) values above 0.150 (the mean O.D. of negative samples plus 6 standard deviations). Negative sera are represented by open symbols.

Panel A illustrates the results obtained using a solid support consisting essentially of only STLV-III-related polypeptide p80 as target antigen.

Panel B illustrates the results obtained using a solid support consisting essentially of a combination of the HIV-1-related polypeptides (III) and (IV) as target antigen.

DETAILED DESCRIPTION OF THE INVENTION

A. Definitions

Amino Acid: All amino acid residues identified herein are in the natural L-configuration. In keeping with standard polypeptide nomenclature, *J. Biol. Chem.*, 243:3557–59, (1969), abbreviations for amino acid residues are as shown in the following Table of Correspondence:

TABLE OF CORRESPONDENCE

| SYMBOL | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Try | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a further sequence of one or more amino acid residues up to a total of about fifty residues in the polypeptide chain.

Polypeptide and peptide: Polypeptide and peptide are terms used interchangeably herein to designate a linear series of no more than about 50 amino acid residues connected one to the other by peptide bonds between the alpha-amino and carboxy groups of adjacent residues.

Protein: Protein is a term used herein to designate a linear series of greater than 50 amino acid residues connected one to the other as in a polypeptide.

B. Polypeptides

All of the polypeptides described herein are characterized as including a specific amino acid residue sequence because in each case that particular sequence has been discovered to be capable of immunologically mimicking a linear or continuous antigenic determinant.

In addition, all of the polypeptides of the present invention contain no more than about 50, more usually fewer than about 35 and preferably fewer than about 25 amino acid residues. The specification of an upper limit of amino acid residues included in the subject polypeptides is dictated by and directly dependent on the amount of immunologic site specificity desired and does not, as is well known in the art, reflect the need for any residues other than the specifically identified sequence to form the defined linear antigenic determinant that is useful herein. Thus, while additional amino acid residues included as a sequence flanking a specifically identified sequence would typically reduce site specificity because they impart the ability to form additional linear antigenic determinants, such additional sequences do not prevent formation of the desired linear antigen determinant that is useful in the present invention.

The peptides of the invention contain at least one cysteine residue, and in certain instances two of such residues. Accordingly, the subject peptides can exist in various oxidative forms. In addition to the monomeric form in which the sulfhydryl group of the cysteine residue(s) is reduced, there can also exist dimeric or polymeric forms in which sulfhydryl groups on two or more peptide molecules become oxidized and form inter- and intrapeptide disulfide bonds. While subject peptides that possess only one cysteine residue can form only linear dimers, those that possess two cysteine residues can form cyclic monomers or linear or cyclic dimers and linear polymers of various lengths. These various oxidative forms are considered part of the subject invention and are included in the terms "polypeptides" and "peptides".

A polypeptide of the present invention can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated hereinby reference. Appropriate protective groups usable in such synthesis are described in the above texts and in J. F. W. McOmie, "Protective Groups in Organic Chemistry", Plenum Press, New York, 1973, which is incorporated herein by reference.

In general, these methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

1. STLV-III-Related Polypeptides

A STLV-III-related polypeptide of the present invention contains at least 7, preferably at least 12, amino acid residues and includes an amino acid residue sequence represented by the formula:

—CAFRQVC—.

In addition, a STLV-III-related polypeptide of the present invention is characterized by its ability to immunoreact with antibodies induced by a HIV-2 TMP, and preferably, induce antibody molecules that immunoreact with native HIV-2 virus.

Preferred STLV-III-related polypeptides contain no more than 33 amino acid residues, have as part of their amino acid residue sequence the sequence —CAFRQVC— and are homologous, preferably without insertion or deletion, and more preferably are identical, to a portion of the sequence shown in FIG. 1. Thus, preferred STLV-III-related polypeptides are thoseconsisting essentially of at least 7 amino acid residues and no more than about 50 amino acid residues. From FIG. 1 it can be seen that the sequence —CAFRQVC— corresponds in sequence, from left to right and in the direction from amino-terminus to carboxy-terminus, to position 17 through position 23 of the amino acid residue sequence shown in FIG. 1. Thus, a preferred polypeptide can include at its amino-terminus zero to 16 contiguous amino acid residues of as shown in FIG. 1 from position 1 through position 16, as well as including at its carboxy-terminus zero to 10 contiguous amino acid residues as shown in FIG. 1 from position 24 through position 33.

In other words, preferred STLV-III-related polypeptides of the present invention are those defined by the amino acid residue sequence represented by the formula:

—BAFRQVB'—;

wherein B is a sequence of amino acid residues selected from the group consisting of:

AIEKYLEDQAQLNAWGC,
IEKYLEDQAQLNAWGC,
EKYLEDQAQLNAWGC,
KYLEDQAQLNAWGC,
YLEDQAQLNAWGC,
LEDQAQLNAWGC,
EDQAQLNAWGC,
DQAQLNAWGC,
QAQLNAWGC,
AQLNAWGC,
QLNAWGC,
LNAWGC,
NAWGC,
AWGC,
WGC,
GC, and
C; and wherein B' is a sequence of amino acid residues selected from the group consisting of:

CHTTAVPWPNAS,
CHTTAVPWPNA,
CHTTAVPWPN,
CHTTAVPWP,
CHTTAVPW,
CHTTAVP,
CHTTAV,
CHTTA,
CHTT,
CHT,
CH, and
C.

In more preferred embodiments, a STLV-III-related polypeptide of the present invention includes an amino acid residue sequence represented by the formula:

—AWGCAFRQVC—.

Most preferably, a STLV-III-related polypeptide of the present invention includes an amino acid residue sequence selected from the group consisting of:

—AIEKYLEDQAQLNAWCAFRQVC—,
—AWCAFRQVCHTTVPWPNAS—,
—AIEKYLEDQAQLNAWGCAFRQVC—,
—AVEKYLKDQAQLNAWGCAFRQVC—,
—AIEKYLKDQAQLNSWGCAFRQVC—,
—SWGCAFRQVCHTSVPWVNDT—,
—AWGCAFRQVCHTTVPWPNAS—,
—AWGCAFRQVCHITVPWPNAS—, and
—CAFRQVC—.

Most preferred specific STLV-III-related polypeptides include those whose amino acid residue sequences are shown in Table 1.

TABLE 1

| Designation | Amino Acid Residue Sequence |
|---|---|
| p80 | AIEKYLEDQAQLNAWCAFRQVC |
| p81 | AWCAFRQVCHTTVPWPNAS |
| p82 | AIEKYLEDQAQLNAWGCAFRQVC |
| p83 | AVEKYLKDQAQLNAWGCAFRQVC |
| p84 | AIEKYLKDQAQLNSWGCAFRQVC |
| p85 | SWGCAFRQVCHTSVPWVNDT |
| p86 | AWGCAFRQVCHTTVPWPNAS |
| p87 | AWGCAFRQVCHITVPWPNAS |
| p88 | CAFRQVC |

It should be understood that a polypeptide of the present invention need not be identical to the amino acid residue sequence of STLV-III TMP (gp32), so long as the subject polypeptides include the required sequence and are able to immunoreact with antibodies induced by a HIV-2 TMP. Therefore, a present STLV-III-related polypeptide can be subject to various changes, such as insertions, and deletions. For example, the glycine residue at position 16 in FIG. 1 .has been deleted from polypeptides p80 and p81.

Also contemplated are substitutions of one amino acid for another, either conservative or non-conservative, where such changes provide for certain advantages in their use. Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding activity.

When a polypeptide of the present invention has a sequence that is not identical to the sequence of a native STLV-III-related TMP because one or more conservative or non-conservative substitutions have been made, usually no more than about 30 number percent, more usually no more than 20 number percent, and preferably no more than 10 number percent of the amino acid residues are substituted, except where additional residues have been added at either terminus for the purpose of providing a "linker" by which the polypeptides of this invention can be conveniently affixed to a label or solid matrix, or carrier. Labels, solid matrices and carriers that can be used with the polypeptides of this invention are described hereinbelow.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal-$NH_2$ acylation, e.g., acetylation, or thioglycolic acid amidation, by terminal-carboxlyamidation, e.g., with ammonia, methylamine, and the like.

When coupled to a carrier via a linker to form what is known in the art as a carrier-hapten conjugate, a STLV-III-related polypeptide of the present invention is capable of inducing antibodies that immunoreact with a HIV-2 TMP. In view of the well established principle of immunologic cross-reactivity, the present invention therefore contemplates antigenically related variants of the polypeptides shown in Table 1. An "antigenically related variant" is a polypeptide that contains no more than about 50 amino acid residues, includes the amino acid residue sequence —CAFRQVC—, and is capable of inducing antibody molecules that immunoreact with a polypeptide from Table 1 and a HIV-2 TMP.

2. HIV-1-Related Polypeptides

In one embodiment, a HIV-1-related di-cys polypetpide of the present invention contains at least 7, preferably at least 12, amino acid residues and includes an amino acid residue sequence represented by the formula:

—CSGKLIC—.

In addition, these polypeptides have the capacity to mimic the immunological properties of the HIV-1 TMP protein, including the ability to 1) immunoreact with antibodies induced by native HIV-1, and 2) induce antibodies that immunoreact with native HIV-1.

Preferred HIV-1-related di-cys polypeptides contain no more than 32 amino acid residues, have as a portion of their sequence the sequence —CSGKLIC— and are homologous, preferably without insertion or deletion, to a portion of the sequence shown in FIG. 2. That is, a preferred HIV-1-related di-cys polypeptide is one corresponding in sequence to the sequence shown in FIG. 2 from position 17 to position 23 and including at its amino-terminus a linear, contiguous sequence of 1 to 16 amino acid residues whose sequence is shown in FIG. 12 from position 1 through position 16. In addition, the polypetpide also includes at its carboxy-terminus a linear, contiguous sequence of 1 to 9 amino acid residues whose sequence is shown in FIG. 1 from position 24 through position 32.

Another way of defining preferred HIV-1-related di-cys polypeptides of the present invention is that they include an amino acid residue sequence represented by the formula:

—JSGCLIJ'—;

wherein J is sequence of amino acid residues selected from the group consisting of:

AVERYLKDQQLLGIWGC,
VERYLKDQQLLGIWGC,
ERYLKDQQLLGIWGC,
RYLKDQQLLGIWGC,
YLKDQQLLGIWGC,
LKDQQLLGIWGC,
KDQQLLGIWGC,
DQQLLGIWGC,
QQLLGIWGC,
QLLGIWGC,
LLGIWGC,
LGIWGC,
GIWGC,
IWGC,
WGC,
GC, and
C; and wherein J' is a sequence of amino acid residue selected from the group consisting of:

CTTAVPWNAS,

CTTAVPWNA,

CTTAVPWN,

CTTAVPW,

CTTAVP,

CTTAV,

CTTA,

CTT,

CT, and

C.

Preferably, J is IWGC.

Preferred HIV-1-related di-cys polypeptides include those whose amino acid residue sequences are shown in Table 2.

TABLE 2

| Formula Designation | Amino Acid Residue Sequence |
|---|---|
| (I) | CSGKLIC |
| (II) | IWGCSGKLICTTAVP |
| (III) | IWGCSGKLICTTAVPWNAS |
| (V) | AVERYLKDQQLLGIWGCSGKLICTTAVPWNAS |
| (VII) | LLGIWGCSGKLIC |
| (VIII) | QQLLGIWGCSGKLICTTAVPWNAS |
| (IX) | IWGCSGKLICTTAVPWN |

TABLE 2-continued

| Formula Designation | Amino Acid Residue Sequence |
|---|---|
| (X) | CSGKLICTTAVPWNAS |
| (XII) | AVERYLKDQQLLGIWGCSGKLIC |
| (XIII) | GCSGKLICTTAVPWN |

The present invention further contemplates the discovery that recognition of antibodies to HIV-1 in immunological assays is significantly enhanced if the above described HIV-1-related di-cys polypeptides are used in combination with a second HIV-1-related polypeptide, designated a di-leu polypeptide.

HIV-1-related di-leu polypeptides consist essentially of at least 15 amino acid residues and include an amino acid residue sequence represented by the formula:

—ZLLG(X)WZ'—, wherein X is selected from the group consisting of I,L, M or F;

wherein Z is selected from the amino acid residue sequence of the HIV-1 virus gp41 protein immediately adjacent to the amino-terminal side of the L-leucine residue in the 599th.position of the gp41 protein (amino acid residue 11 of FIG. 2);

wherein Z' is selected from the amino acid residue sequence of the HIV-1 virus gp41 protein immediately adjacent to the carboxy side of the L-tryptophan residue in the 603rd position of the gp41 protein (amino acid residue 15 of FIG. 2); and wherein one of Z or Z' may be zero residues long and wherein Z and Z' together comprise at least ten residues.

Preferred HIV-1-related di-leu polypeptides contain no more than 32 amino acid residues, have as a portion of their sequence the sequence represented by the formula:

—ZLLG(X)WZ'—, and are, except when X is other than I, homologous to a portion of the sequence shown in FIG. 2. Thus, in preferred embodiments, Z is a linear, contiguous sequence of 1 to 10 amino acid residues whose sequence is shown in FIG. 2 from position 1 to position 10, and Z' is a linear contiguous sequence of 1 to 17 amino acid residues whose sequence is shown in FIG. 2 from position 16 to 32. In other words, in preferred embodiments, Z is a sequence of amino acid residues selected from the group consisting of:

AVERYLKDQQ,
VERYLKDQQ,
ERYLKDQQ,
RYLKDQQ,
YLKDQQ,
LKDQQ,
KDQQ,
DQQ,
QQ, and
Q; and Z' is a sequence of amino acid residues selected from the group consisting of:

GCSGKLICTTAVPWNAS,
GCSGKLICTTAVPWNA,

GCSGKLICTTAVPWN,
GCSGKLICTTAVPW,
GCSGKLICTTAVP,
GCSGKLICTTAV,
GCSGKLICTTA,
GCSGKLICTT,
GCSGKLICT,
GCSGKLIC,
GCSGKLI,
GCSGKL,
GCSGK,
GCSG,
GCS,
GC, and
G.

It should be noted that X corresponds to position 602 of the TMP (gp41) protein of HIV-1, and when X is I, the included sequence corresponds in amino acid residue sequence of the HIV-1 TMP protein from position 598 to position 604 i.e., position 10 to position 16 of the polypeptide shown in FIG. 2. On the other hand, it is believed that based on a study of various TMP amino acid residue sequences obtained from different HIV-1 isolates, the substitution for I at position 602 with L, M or F results in an antigenically equivalent polypeptide.

Preferred HIV-I related di-leu polypeptides include those whose amino acid residue sequences are shown in Table 3.

TABLE 3

| Formula Designation | Amino Acid Residue Sequence |
|---|---|
| (IV) | AVERYLKDQQLLGIWGCSGKLI |
| (VI) | LKDQQLLGIWGCSGLKI |
| (XIV) | LKDQQLLGIWGCSGK |
| (XV) | RILAVERYLKDQQLLGIWGCS |

Preferred combinations of HIV-1-related di-cys and di-leu polypeptides include (IV) or (XII) with (III), (XIII), or (X). The combinations of (III) with (IV) and (XIII) with (IV) being particularly preferred the combinations.

In another embodiment, the present invention contemplates a HIV-1-related polypeptide having an amino acid residue sequence represented by the formula, designated formula (XI):

SGKLICTTAVPWNAS.

In view of the results discussed in the Examples, it is clear that a significant antigenic determinant of the HIV-1 virus which reacts with HIV-1 induced antibodies is defined by (contained within) the seven amino acid residue sequence of formula (I) described before. Moreover, even though each of the HIV-1-related polypeptides of the present invention reacts with most HIV-1 positive sera, individual patient sera have been observed to react specifically with one of the HIV-1-related peptides but not another. This observation indicates that additional antigenic determinants exist in longer peptides containing the sequence of formula (I), such as those peptides shown in Table 2. It is well within the skill of an ordinary worker in the peptide synthesis art to prepare fragments of the HIV-1-related peptides to determine antigenic and immunogenic fragments within them. Accordingly, such antigenic and immunogenic fragments can be used in the diagnostic systems and methods of the present invention. Moreover, one of skill would also recognize that longer peptides corresponding to a portion of the HIV-1 TMP protein and conforming to the teachings herein would function in the assay methods and systems of the present invention.

C. Inocula

In another embodiment, a STLV-III-related polypeptide of this invention or an antigenically related variant thereof is used in a pharmaceutically acceptable aqueous diluent composition to form an inoculum that, when administered in an effective amount, is capable of inducing antibodies that immunoreact with STLV-III and HIV-2.

The word "inoculum" in its various grammatical forms is used herein to describe a composition containing a polypeptide of this invention as an active ingredient used for the preparation of antibodies against HIV-2. When a polypeptide is used to induce antibodies it is to be understood that the polypeptide can be used alone, or linked to a carrier as a conjugate, or as a polypeptide polymer, but for ease of expression the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies as already noted.

As also already noted, one or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing 30 conjugates can also be used. Exemplary additional linking procedures include the use of Michael addition reaction products, di-aldehydes such as glutaraldehyde, Klipstein et al., *J. Infect. Dis.*, 147, 318–326 (1983) and the like, or the use of 35 carbodiimide technology as in the use of a water-soluble carbodiimide to form amide links to the carrier. For a review of protein conjugation or coupling through activated functional groups, see Aurameas, et al., *Scand. J. Immunol.*, Vol. 8, Supp-1. 7, 7–23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

D. Antibodies and Antibody Compositions

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules, and those portions of an immunoglobulin molecule that contain the paratope, including those portions known in the art as Fab, Fab', $F(ab')_2$ and F(v).

An antibody composition of the present invention is characterized as containing antibody molecules that immunoreact with HIV-2 TMP and a STLV-III-related polypeptide of this invention, but is substantially free of antibodies that immunoreact with any other HIV-2-related protein.

An antibody composition of the present invention is typically produced by immunizing a laboratory mammal with an inoculum of the present invention and to thereby induce in the mammal antibody molecules having the appropriate polypeptide immunospecificity. The antibody molecules are then collected from the mammal and isolated to the extent desired by well known techniques such as, for example, by immunoaffinity chromatography. The antibody composition so produced can be used in, inter alia, the diagnostic methods and systems of the present invention to detect HIV-2 in a body sample.

The antibody compositions of this invention induced by a polypeptide of this invention, including an oligomeric polypeptide and a polypeptide polymer, can be described as being oligoclonal as compared to naturally cocurring polyclonal antibodies since they are raised to an immunogen (the relatively small polypeptide) having relatively few epitopes as compared to the epitopes mimicked by an intact HIV-2

TMP molecule. Consequently, receptors of this invention bind to epitopes of the polypeptide, whereas naturally occurring antibodies raised to the whole TMP molecule bind to epitopes throughout the TMP molecule and are referred to as being polyclonal.

Monoclonal antibody compositions are also contemplated by the present invention. A monoclonal antibody composition contains, within detectable limits, only one species of antibody combining site capable of effectively binding HIV-2 TMP. Thus, a monoclonal antibody composition of the present invention typically displays a single binding affinity for HIV-2 TMP even though it may contain antibodies capable of binding proteins other than HIV-2 TMP.

Suitable antibodies in monoclonal form, typically whole antibodies, can also be prepared using hybridoma technology described by Niman et al., *Proc. Natl. Sci., U.S.A.*, 80:4949–4953 (1983), which description is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a polypetpide of this invention.

It is preferred that the myeloma cell line be from the same species as the lymphocytes. Typically, a mouse of the strain 129 $GlX^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas secreting the receptor molecules of this invention are identified using the enzyme linked immunosorbent assay (ELISA) described in Example 11.

A monoclonal antibody composition of the present invention can be producedby initiating a monoclonal hybridoma culture comprising a nutrient medium containing a hybridoma that secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/1 glucose, 20 mm glutamine, and 20% fetal calf serum. An exemplary inbred mouse strain is the Balb/c.

The monoclonal antibody compositions produced by the above method can be used, for example, in diagnostic and therapeutic modalities wherein formation of an HIV-2 TMP-containing immunoreaction product is desired.

E. Diagnostic Systems

A diagnostic system in kit form of the present invention includes, in an amount sufficient for at least one assay, a polypeptide, antibody composition or monoclonal antibody composition of the present invention, as a packaged reagent. Instructions for use of the packaged reagent are also typically included.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An examplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emited produce gamma rays upon encounters with electrons present in the animal's body. Also useful is a beta emitter, such $^{111}$indium of $^3H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the presence or quantity of at least anti-HIV-2 antibodies in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; No. 3,850,752; and No. 4,016,043, which are all incorporated herein by reference.

Thus, in preferred embodiments, a polypeptide, antibody molecule composition or monoclonal antibody molecule composition of the present invention can be affixed to a solid matrix to form a solid support that comprises a package in the subject diagnostic systems.

The reagent is typically affixed to the solid matrix by adsorption from an aqueous medium although other modes of affixation, well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

In one embodiment a diagnostic system of the present invention is useful for assaying for the presence of antibodies induced by HIV-2. Such a system comprises, in kit form, a package containing a STLV-III-related polypeptide of this invention. Preferably, the included STLV-III-related polypeptide contains no more than 33 amino acid residues and has a sequence homologous to a portion of the sequence shown in FIG. 1. More preferably, the polypeptide is p80, p81, p82, p83, p84, p85, p86, p87, p88, or p89, most preferably p82 and/or p86, all of whose sequences are shown in Table 1.

When it is desired to provide a diagnostic system capable of being used to detect and distinguish between exposure to HIV-1 and HIV-2, a HIV-1-related di-cys or di-leu polypeptide as described herein is included along with a STLV-III-related polypeptide in the kit. Preferred HIV-1-related di-cys polypeptides included in the kit are those that contain no more than 32 amino acid residues, have as a portion of their sequence the sequence —CSGKLIC— and are homologous to a portion of the sequence shown in FIG. 2. More preferably, an included HIV-1-related di-cys polypeptide has a sequence selected from the group shown in Table 2.

In another embodiment of a diagnostic system capable of being used to detect and distinguish between anti-HIV-1 and anti-HIV-2 antibodies, a HIV-1-related di-leu polypeptide of this invention is included in the kit, in addition to the STLV-III-related polypeptide. Preferred HIV-1-related di-leu polypeptides included in the kit are those that contain no more than 32 amino acid residues, have as a portion of their sequence the sequence represented by the formula:

—ZLLG(X)WZ—, and are, except when X is other than I, homologous to a portion of the sequence shown in FIG. 2. More preferably, the HIV-1-related di-leu polypeptide has a sequence selected from the group shown in Table 3.

In view of the finding that a combination, in admixture, of HIV-1 di-cys and di-leu polypeptides of the present invention unexpectedly allows for an increased ability to detect exposure to HIV-1, a diagnostic system comprising a package that includes a STLV-III-related polypeptide of this invention and a combination, in admixture, of a HIV-1 di-cys and a HIV-1 di-leu polypeptide is also contemplated.

In one embodiment, the STLV-III-related polypeptide and HIV-1-related polypeptide combination are physically separated within the kit thereby allowing for distinguishing between the presence of anti-HIV-1 and HIV-2 antibodies. An exemplary kit of this type includes a first solid support comprised of microtiter plate wells coated with, i.e., having operatively affixed thereto, a STLV-III-related polypeptide, preferably p82 and/or p86, and a second solid support comprised of microtiter plate wells coated with, i.e., having operatively affixed thereto an admixture of HIV-1-related polypeptides (III) and (IV). Of course, the STLV-III and HIV-1 polypeptide coated wells can be on the same or different plates.

In another embodiment, the STLV-III-related, HIV-1-related di-cys and HIV-1-related di-leu polypeptides are included in the kit as an admixture of all three, thereby creating the ability to screen for exposure to a greater range of AIDS-related viruses using one solid support. A kit of this type typically comprises a solid support such as a microtiter plate having operatively affixed thereto in an individual well, an admixture of STLV-III-related polypeptide, preferably p82 and/or p86, HIV-1-related di-cys polypeptide (III) and HIV-1-related di-leu polypeptide (IV).

F. Assay Methods

The present invention contemplates a method for detecting the presence and preferably amount of antibodies against HIV-2 (AIDS-related West African retroviruses) in a body fluid sample by producing a complex containing a polypeptide of the present invention and such antibodies. Those skilled in the art will understand that there are numerous well known clinical diagnostic chemistry procedures that can be utilized to form those complexes. Thus, while exemplary assay methods are described herein, the invention is not so limited.

Various heterogeneous and homogeneous assay protocols can be employed, either competitive or non-competitive, for detecting the presence, and preferably amount, of antibodies against HIV-2 TMP in a body fluid sample using the STLV-III-related polypeptides of this invention. For example, the present invention contemplates a method for assaying a body sample for the presence of anti-HIV-2 antibodies comprising the steps of:

(a) Admixing a body fluid sample with a STLV-III-related polypeptide of the present invention, preferably p82 and/or p86, thus forming an immunoreaction admixture. Preferably, the body fluid sample is provided as a known amount of blood or a blood derived product such as serum or plasma, although urine, saliva, semen, vaginal secretion or cerebral-spinal fluid (CSF) can also be used. Preferably the HIV-2-related polypeptide is present as part of a solid support, e.g., a HIV-2 related polypetpide of the present invention affixed to the inner walls of microtiter plate well, so that the immunoreaction admixture formed has a solid and a liquid phase.

(b) Maintaining the admixture under biological assay conditions for a predetermined time period such as about 10 minutes to about 16–20 hours at a temperature of about 4 degrees C. to about 45 degrees C. that is sufficient for any anti-HIV-2 antibodies present in the sample to immunoreact with (immunologically bind) the polypeptide to form a polypeptide-containing immunoreaction product.

Biological assay conditions are those that maintain the biological activity of the polypeptide molecules of this invention and the anti-HIV-2 antibodies sought to be assayed, and include a temperature range of about 4 degrees C. to about 45 degrees C., a pH value range of about 5 to about 9 and an ionic strength varying from that of distilled water to that of about one molar sodium chloride. Methods for optimizing such conditions are well known in the art.

(c) Assaying for the presence of any polypeptide-containing immunoreaction product that formed, and thereby the presence of any anti-HIV-2 antibodies in the immunoreaction admixture is also determined. Preferably, the amount of any polypeptide-containing immunoreaction product formed is determined, and thereby the amount of anti-HIV-2 antibodies present in the sample.

Assaying for the presence of any polypeptide-containing (anti-HIV-2 antibody-containing) immunoreaction product, either directly or indirectly, can be accomplished by assay techniques well known in the art. For instance, in preferred embodiments, the polypeptide-containing immunoreaction product of step (b) is further prepared for assaying according to step (c) by the following steps:

(i) Admixing a biologically active labeled specific binding agent with the polypeptide-containing immunoreaction product to form a labeling-reaction admixture. The labeled specific binding agent is capable of binding to any immunoglobulin present in the polypeptide-containing immunoreaction product to form a labeled complex. Preferably, the labeled specific binding agent is comprised of second antibody molecules such as xenogeneic anti-human Fc antibodies. More preferably, the labeled specific binding reagent is immunoglobulin class specific.

(ii) The labeling-reaction admixture so formed is maintained under biological assay conditions for a predetermined time period sufficient for the labeled specific binding agent to bind to any anti-HIV-2 antibodies present as polypeptide-containing immunoreaction product to form a labeled complex.

Assaying for the presence of the labeled complex provides an assay for the presence of anti-HIV-2 antibodies in the sample. In preferred embodiments, the amount of the labeled specific binding agent bound as part of the complex is determined, and thereby the presence and amount of anti-HIV-2 antibodies in the sample can be determined. That amount can be zero, thereby indicating no anti-HIV-2 antibodies are present in the sample, within the limits that can be detected. Methods for assaying for the presence and amount of a labeled specific binding agent depend on the label used, such labels and assay methods being well known in the art.

Alternatively, homogeneous assay methods such as those described in U.S. Pat. Nos. 4,536,479; No. 4,233,401; No. 4,233,402 and No. 3,996,345, whose disclosures are incorporated herein by reference, can be used to detect the polypeptide-containing immunoreaction product of step (c).

EXAMPLES

The following examples are intended to illustrate, but not limit, the present invention.

1. Synthesizing HTLV-III Peptide (II)

A. Synthesis of BOC-Proline Resin:

Chloromethylated styrene-divinylbenzene polymer containing 1.3 molar equivalents (meq) chloride/gram of resin was esterified with Boc-proline in anhydrous N,N-Dimethylformamide (DMF) using potassium iodide (KI) as the catalytic agent. The reaction was carried out at 55° C. for 24 hours as described by Steward & Young, "Solid Phase Peptide Synthesis", 2nd edition (1984), Pierce Chemical Co. The substitution of Boc-proline was 0.92 mMole/gram as determined using a picric acid assay on a portion of deblocked resin.

B. Synthesis and Characterization of Peptide (II).

Synthesis of peptide of formula (II) was accomplished using the technique of Merrifield, *J. Am. Chem. Soc.*, 85:2149–54 (1963). The peptide sequence IWGCSGKLICT-TAVP was synthesized on a Vega 250C automated peptide synthesizer using a double couple program. Boc-proline resin (1.8326 g) was sequentially double coupled with the following Boc-L-amino acids obtained from Bachem. Inc., Torrence, Calif., in twelve meq excess:

| Amino Acid | Solvent |
|---|---|
| Boc—Val | $CH_2Cl_2$ |
| Boc—Ala | $CH_2Cl_2$ |
| Boc—(O-Bzl)—Thr | $CH_2Cl_2$ |
| Boc—(O-Bzl)—Thr | $CH_2Cl_2$ |
| Boc—(MeOBzl)—Cys | $CH_2Cl_2$ |
| Boc—Ile | $CH_2Cl_2$ |
| Boc—Leu | 10% DMF/$CH_2Cl_2$ |
| Box—(Cl-Z)—Lys | $CH_2Cl_2$ |
| Boc—Gly | $CH_2Cl_2$ |
| Boc—(O-Bxl)—Ser | $CH_2Cl_2$ |
| Boc—(MeOBzl)—Cys | $CH_2Cl_2$ |
| Boc—Gly | $CH_2Cl_2$ |
| Boc—Trp | 10% DMF/$CH_2Cl_2$ |
| Boc—Ile | $CH_2Cl_2$ |

In the above sequential addition protocol, "Boc" is used as a chemical abbreviation for the tert-butyloxcarbonyl alpha-amino protecting group. The functional group is removed by hydrolysis in 50% trifluoroacetic acid (TFA)/ 50% dichloromethane ($CH_2Cl_2$) after the amino acid has been coupled to the growing peptide chain. This action exposes the amino terminus of the chain to allow the next amino acid to be effectively coupled.

In addition to the Boc protecting group on every amino acid, the side chains of some amino acids are further protected from reaction by the chemistry of peptide synthesis. These protecting groups, listed in parentheses on the foregoing sequential addition list, are all stable to the conditions of peptide synthesis, yet are easily removed from the amino acid during cleavage in hydrofluoric acid. Anisole (methylphenyl ether) acts as a nucleophilic scavenger during the HF cleavage step to prevent alkylation of the peptide by the liberated protecting group carbonium ions. The protecting groups for the amino acids listed are defined below:

O-Benzyl:Benzyl-ester; attached to the hydroxyl side chain of both serine and threonine to prevent the acylation or branching of the peptide chain.

MeObzl:4-Methoxybenzyl; attached to the sulfhydryl group of cysteine to prevent its oxidation during peptide synthesis.

Cl-Z:2-chlorobenzyloxycarbonyl; attached to the alpha-amino group of lysine to prevent the formation of side chain growth from this site on the peptide.

The peptide was cleaved from the resin with 10% anisole in hydrofluoric acid and extracted with 20% aqueous acetic acid. This solution was filtered to remove solid resin and run through a Fractogel TSK HW-40F desalting column using an eluent of 20% aqueous acetic acid. Fractions were collected in 10 ml aliquots and the column effluent was monitored at 280 nanometers (nm). Fractions showing positive absorbance at 280 nm were diluted with 0.1% trifluoracetic acid (TFA) in water and analyzed by high performance liquid chromatography (HPLC) using the following analytical HPLC conditions:

Buffer A:0.1% TFA/distilled deionized water;

Buffer B:0.1% TFA/HPLC grade acetonitrile;

Gradient Conditions:10% buffer 'B' to 50% buffer 'B' in buffer "A" over 20 minutes;

Wavelength:214 nm;

Flow:1.0 ml/minute (min);

Column:Vydac 214TP54 C-4 Protein column, 250×4.5 min.

The major peak of absorbance at 214 nm was determined to have a retention time of 12.42 min. The Fractogel fractions that contained greater than 70% of this peak were pooled and labeled Fr:1. The Fractogel fractions that contained less than 70% but greater than 50% of this peak were pooled and labeled Fr:2.

Analytical HPLC on Fr:1 showed the 12.42 min peak to constitute 87% of the total area. Fr:1 was further characterized by amino acid analysis using a model 4150 Alpha Amino Acid Analyzer, LKB Instruments, Inc. Gaithersburg, Md., amino acid residue sequence determination using a model 470 A Protein sequencer, Applied Biosystems, Foster City, Calif., and determination of % peptide content as determined from the recovery on amino acid analysis of a known amount of peptide. Peptide sequence analysis was also performed on the peptide-resin to confirm the expected sequence of the peptide.

C. Polymerization of the Peptide of Formula (II):

The peptide contained in the Fr:1 pool described in part B was lyophilized to remove acetic acid and solubilized at 200 ug/ml in 0.1M sodium bicarbonate buffer pH 9.0. Aliquots of this peptide diluted to 20 micrograms per milliliter (ug/ml) in sodium bicarbonate buffer were used to coat microtiter walls for ELISAs shown in Table 4. For assays shown below in Tables 4–6, the peptide was solubilized in water at 10 milligrams per milliliter (ug/ml) and diluted in phosphate buffer pH 7.3 to 5 ug/ml for coating microtiter wells.

The peptide in Fr:1 exists primarily in a single form that is believed to be unoxidized monomer. Because the peptide of formula (II) contains two cysteines, however, it polymerizes in the presence of air upon solubilization in neutral or basic aqueous buffer.

The peptide used in ELISAs described below is a mixture of very small amounts of linear monomer, and larger amounts of cyclic monomer (formed by intrapolypeptide disulfide bonding) and even larger amounts of polymers (formed by interpolypeptide disulfide bonding) of various sizes. Without wishing to be bound thereby, applicants believe that the polymer forms are important for the reactivities described herein. The cyclic monomer form, while retaining a portion of the antigenicity of the polymer form, is believed to be less efficient in binding to the microtiter wells and is less suited as the solid phase component of the ELISA. The presumed cyclic monomer is revealed as a sharp peak at about 12.7 min retention time in HPLC analysis while the polymer is characterized as a broad peak at approximately 15.9 min retention time.

Oxidation conditions can be altered with respect to temperature, pH, peptide concentration, and the like as known to those skilled in the art to alter the proportion of monomer, cyclic monomer and polymer remaining in the preparation, or the size of polymers formed. Small amounts of so called deletion peptides (lacking one or more amino acids) and their oxidation forms can also be found in the peptide preparations used in the ELISA but these minor impurities do not affect the use of the peptide.

2. Synthesis and Characterization of HIV-1 Polypeptides (III) through (XI):

Synthesis of these peptides was accomplished using substantially the same classical Merrifield technique as described earlier for peptide (II). For peptide (III), Boc-serine resin with substitution of 0.92 mMole/gram was used. For peptide (IV), Boc-isoleucine resin with substitution of 0.8 mMole/gram was used. Synthesis of the Boc-serine and Boc-isoleucine resins was accomplished by the Gisin method as described by Stewart & Young, supra.

A. For peptide (III) the amino acid residue sequence IWGCSGKLICTTAVPWNAS was synthesized using the following Boc-L-amino acids in 12 meq excess:

| Amino Acid | Solvent |
|---|---|
| Boc—Ala | $CH_2Cl_2$ |
| Boc—Asn/Hobt | DMF |
| Boc—Trp | 10% DMF/$CH_2Cl_2$ |
| Boc—Pro | $CH_2Cl_2$ |
| Boc—Val | $CH_2Cl_2$ |
| Boc—Ala | $CH_2Cl_2$ |
| Boc—(O-Bzl)—Thr | $CH_2Cl_2$ |
| Boc—(O-Bzl)—Thr | $CH_2Cl_2$ |
| Boc—(MeoBzl)—Cys | $CH_2Cl_2$ |
| Boc—Ile | $CH_2Cl_2$ |
| Boc—Leu | 10% DMF/$CH_2Cl_2$ |
| Boc—(Cl-Z)—Lys | $CH_2Cl_2$ |
| Boc—Gly | $CH_2Cl_2$ |
| Boc—(O-Bzl)—Ser | $CH_2Cl_2$ |
| Boc—(MeOBzl)—Cys | $CH_2Cl_2$ |
| Boc—Gly | $CH_2Cl_2$ |
| Boc—Trp | 10% DMF/$CH_2Cl_2$ |
| Boc—Ile | $CH_2Cl_2$ |

B. For peptide (IV) the peptide sequence AVERYLKDQQLLGIWGCSGLKI was synthesized using the following Boc-L-amino acids in 12 meq excess:

| Amino Acid | Solvent |
|---|---|
| Boc—Leu | 10% DMF/$CH_2Cl_2$ |
| Boc—(Cl-Z)—Lys | $CH_2Cl_2$ |
| Boc—Gly | $CH_2Cl_2$ |
| Boc—(O-Bzl)—Ser | $CH_2Cl_2$ |
| Boc—(MeOBzl)—Cys | $CH_2Cl_2$ |
| Boc—Gly | $CH_2Cl_2$ |
| Boc—Trp | 10% DMF/$CH_2Cl_2$ |
| Boc—Ile | $CH_2Cl_2$ |
| Boc—Gly | $CH_2Cl_2$ |
| Boc—Leu | 10% DMF/$CH_2Cl_2$ |
| Boc—Leu | 10% DMF/$CH_2Cl_2$ |
| Boc—Gln/Hobt | DMF |
| Boc—Gln/Hobt | DMF |
| Boc—(Bzl)—Asp | $CH_2Cl_2$ |
| Boc—(Cl-Z)—Lys | $CH_2Cl_2$ |
| Boc—Leu | 10% DMF/$CH_2Cl_2$ |
| Boc—(Br-Z)—Tyr | $CH_2Cl_2$ |
| Boc—(Tosyl)—Arg | 10% DMF/$CH_2Cl_2$ |
| Boc—(Bzl)—Blu | $CH_2Cl_2$ |
| Boc—Val | $CH_2Cl_2$ |
| Boc—Ala | $CH_2Cl_2$ |

As with peptide (II), in addition to the Boc protecting group on every amino acid, the side chains of some amino acids are further protected from reaction by the chemistry of peptide synthesis. In addition to those protecting groups described for the amino acids in the peptide (II) synthesis, the following protecting groups for the amino acids unique to peptides (III) and (IV) were used:

Hobt:1-hydroxybenzotriazole; used in equimolar amounts to glutamine and asparagine during coupling to prevent dehydration to the nitrile forms.

Tosyl:p-toluene sulfonyl; used to acylate the guanidine group in the side chain of arginine.

Bzl:beta-benzyl ester; blocks the carboxyl groups in the side chain of aspartic acid and glutamic acid.

BrZ; 2-bromobenzyloxyarbonyl; blocks the hydroxyl group in the side chain of tyrosine.

Peptides were cleaved from the resin, filtered, extracted with acetic acid and run through a Fractogel desalting column as in Example 1. For peptide (IV), Fractogel fractions were analyzed by analytical HPLC and fractions containing at least 30% of the total absorption at 214 nm as the major peak migrating at approximately 14 minutes retention time were pooled. The pooled fractions were chromatographed on carboxymethyl cellulose equilibrated with 0.01 M ammonium acetate, pH 4.4. The column was eluted with a step gradient of ammonium acetate and the fraction eluting at 0.2M ammonium acetate was collected, lyophilized, and analyzed by analytical HPLC. The major peak migrating at 15 minutes retention time comprised between 30% and 40% of the total absorption at 214 nm and the material had an acceptable amino acid content. This material was resolubilized and used in ELISA as described for peptide (II).

For peptide (III), Fractogel fractions were likewise analyzed by analytical HPLC. Fractions containing at least 70% of the total absorption at 214 nm as the major peak migrating at approximately 12.99 minutes retention time were pooled, lyophilized, and analyzed by HPLC and for amino acid content. This material was resolubilized and used in ELISA as described for peptide (II).

When used in combination as the solid phase component in an ELISA, 1 microgram of peptide (III) and 0.5 micrograms of peptide (IV) were used per microtiter well. The peptide was either dried onto the well at 37° C. or "wet packed" onto the plate by incubation overnight at 4° C.

C. For peptide (V), Boc-serine resin was used as described for synthesis of peptide (III). Synthesis of (V) proceeded as described for synthesis of (III) through the addition of the C-terminal isoleucine of peptide (III). From that point on, for completion of the (V) sequence, the procedure for addition of the amino acids in the sequence AVERYLKDQQLLG in peptide (IV) was followed.

Peptide (V) was cleaved from the resin, filtered, extracted with acetic acid and run through a Fractogel fractions containing the major peak of absorption at 280 nm were pooled and labeled Fr:1. Fr:1 was analyzed for amino acid content and found to be acceptable. This fraction was lyophilized and used in ELISA as described for peptide (II).

D. Following similar procedures the peptides of formulas (I), (VI) through (XVI) were prepared.

E. Peptides (I) through (III), (V), and (VII) through (X) contain two cysteines. Accordingly, these peptides can polymerize and cyclize through oxidative disulfide bonding using atmospheric oxygen as the oxident. The addition of the four amino acid residues at the C-terminal end of (III) apparently assist the cyclic form of the peptide in binding to the plastic in the ELISA assay. As a result, the cyclic form of (III) is more effective in solid phase ELISA than is (II) cyclic. The forms of the (II), (III) and (V) peptides used thus far in ELISA to assay for HIV-1 antibody recognition have been typically a mixture of linear monomer, cyclic monomer, dimer and polymer.

Peptides (IV), (VI) and (XI) contain only one cysteine. These peptides can form a dimer structure through disulfide bonding.

Under conditions of solubilization of peptides in preparation for ELISA (e.g., 0.1M sodium bicarbonate buffer at pH 9.0 in the presence of air and its oxygen) most of the sulfhydryl groups of peptides (II), (III), (IV), and (V) have been converted to the disulfide form.

3. preparation of Comparative HTLV-III Peptides

Following similar procedures to those of Examples 2 and 3, for comparative purposes, peptides having the following formulae were synthesized:

| SEQUENCE | DESIGNATION |
|---|---|
| QLQARILAVERY | (C-I) |
| AVERYLKDQQLLG | (C-II), |
| LKDQQLLGIWGCS | (C-III), |
| IWGCSGKLI | (C-IV), and |
| LICTTAVPWNASWSN | (C-VIII). |

These peptides each have sequences corresponding to the sequence of the HIV-1 envelope but are neither the di-cys nor di-leu polypeptides described previously. Specifically, peptides having the formula (C-I) and (C-II) are sequences upstream from the amino end of the sequence of formula (I) i.e., CSGLKIC. Peptides having the formula (C-III) contain only the amino terminal portion of the sequence of formula (I). Peptides having the formula (C-IV) contain the full sequence of formula (I), but for the carboxy-terminal L-cys residue. As will be described herein, each of these peptides fails to exhibit the desirable immunoreactive properties.

4. preparation of HIV-1 ELISA Assay Kit and Procedure for Use:

A. Procedure #1 for HIV-1 ELISA (1) coat ELISA plate with peptide-1 ug/50ul/well in 0.1M $NaHCO_3$, pH 9;

(2) let plates dry overnight uncovered at 37° C.; then wash with PBS;

(3) block plates with 300 ul/well of blocking buffer (5% NCS-PBS) for 2 hrs. at 37° C.;

(4) shake out blocking buffer and drain well;

(5) add 50 ul/well test antiserum (first antibody) for 30 to 120 minutes at 37° C. (If the antiserum is to be diluted, use T-wash.) Dilutions of 1:2 to 1:100 have been used;

(6) shake out test antisera and wash plate six times with PBS-Tween20;

(7) add 100 ul/well of labeled specific binding agent in the form of a enzyme-labeled second antibody diluted 1:4000 with T-wash. Maintain 30 to 120 minutes at 37° C.;

(8) shake out any unreacted second antibody and wash plate six times with PBS-Tween20;

(9) add 100 ul/well OPD substrate (or 5 ul ABTS solution) for 20 minutes at RT;

(10) add 50 ul/well of 4N $H_2SO_4$ to stop OPD reaction (or 100 ul/well of 1% SDS for ABTS reaction);

(11) read plate on an MR 500 Microplate ELISA plate reader. (490 nm for OPD or 405 nm for ABTS).

Reagents:

(1) 0.1M $NaHCO_3$ pH9;

(2) NCS-PBS:phosphate buffered saline (PBS) containing 5% normal calf serum;

(3) T-wash:(780 ml TBS+20 ml NCS+1.6 g bovine serum albumin (BSA)+0.4 ml polyoxyethylene (20) sorbitan monolaurate (Tween20); TBS:12.11g Tris Base 17.5g NaCl 1800ml H2O pH to 7.6 with HCl (CA.3N) final volume at 2000 ml.

(4) Washing buffer PBS-Tween20:0.5ml Tween 20 per liter PBS;

(5) OPD substrate:one o-phenylenediamine (OPD) tablet/3 ml H2O/1.24 ul 30% $H_2O_2$;

(6) 4N $H_2SO_4$;

(7) ABTS:$H_2O_2$ in 1:1 ratio by volume of solutions supplied by Kirkegaard and Perry Laboratories, Inc., Gaithersbury, Md.) ABTS=2,2'-azino-di-[3-ethyl-benzthiazoline sulfonate];

(8) 1% SDS:1% sodium dodecyl sulfate.

The material used in step 1 for coating the ELISA plate is a peptide of formula (II), (III), (IV), (V) or a mixture thereof as described above. The second antibody is either a commercially-available peroxidase-labeled, polyclonal anti-human immunoglobulin antibody (Cappel Laboratories Catalog No. 3201-0231; Peroxidase-conjugated IgG fraction of goat anti-human immunoglobulins) or a peroxidase-labeled mouse monoclonal anti-human IgG antibody (Ortho Diagnostics, Inc., Raritan, N.J.), or a mixture of peroxidase-labeled mouse monoclonal anti-human IgG, IgA and IgM antibodies.

B. Procedure #2 for HIV-1 ELISA Tables 10 and 13):

(1) Coat ELISA plate with peptides—1.0 ug peptide IV, 0.5 ug peptide III 200 ul/well in 0.1M carbonate buffer, pH 9.6;

(2) incubate plates overnight at 4° C.;

(3) block plates with 300 ul/well 1.0% BSA-PBS plus additives for 1.5 hr at 37° C.;

(4) shake out blocking buffer;

(5) dry plates for 1.0 hr at 37° C.;

(6) add 200 ul/well 1% bovine gamma globulin—5% BSA-0.5% Tween 20-PBS, pH 7.2;

(7) add 20 ul/well test sera, incubate 30 min at 37° C.;

(8) shake out test sera, wash plate 5x with PBS-0.5% Tween 20.

(9) add 200 ul/well horseradish peroxidase labeled monoclonal anti-human IgG diluted 1:3500 with 50% fetal calf serum-1% horse serum-0.5% Tween-PBS;

(10) incubate 30 min at 37° C.;

(11) shake out labeled monoclonal anti-human IgG, wash plate 5x with PBS-0.05% Tween 20;

(12) add 200 ul/well OPD substrate and incubate for 30 min at room temperature;

(13) add 50 ul/well 4N $H_2SO_4$ to stop reaction;

(14) Read plate at 490 nm in MR 500 Microplate Reader.

Reagents:

(1) Phosphate Buffered Saline (PBS) pH 7.3;

8.0 g of sodium chloride;

0.2 g of potassium phosphate, monobasic;

1.16 g of sodium phosphate, dibasic;

0.2 g of potassium chloride;

0.2 g of thimerosal;

water to 800 ml and mix, adjust pH if necessary;

add water to 1L.

(2) Coating Buffer: pH 9.6, 0.01M carbonate buffer.

(3) Blocking buffer is PBS containing the following additives:

1% bovine serum albumin (Sigma #A7030);

10 Ku/ml Aprotinin;

10 ug/ml trypsin inhibitor;

10 mMEACA (E-amino caproic acid);

0.5 MM PMSF (phenyl-methyl-sulfonyl fluoride);

2.0 mMEDTA;

10% glycerol;

(4) Specimen Diluent:

10.0 g Bovine Gamma Globulin, Fraction II, lyophilized;

50.0 g Bovine Albumin, Fraction V;

0.5 ml Polysorbate 20 (Tween20);

Add water to 1 L and mix;

Filter through 0.2 micron filter.

(5) Conjugate Diluent:

490 ml PBS;

500 ml heat inactivated fetal bovine serum;

10 ml heat inactivated horse serum;

0.1 g thimerosal;

0.329 g potassium ferricyanide;

add water to 1 L mix;

filter through 0.2 micron filter.

5. Evaluation of HIV-1 Peptide II Based ELISA

The ELISA kits described in Example 4A made with peptide (II) were evaluated against a panel of sera comprising sera from normal subjects, patients with disorders or diseases unrelated to AIDS, known AIDS patients, known ARC patients, and patients whose diagnosis is unknown but who are antibody-positive for HIV-2 antibodies by commercial tests or by Western blot assay. The results are summarized in Tables 4–7. For comparison, these same sera samples were assayed with commercially available kits that utilize a viral lysate as antigen and by Western blot assay. The commercial kits selected for these studies were from Abbott Laboratories, North Chicago, Ill. and Electro-Nucleonics, Inc. (ENI), Columbia, Md., and the directions supplied with each commercial kit were followed in carrying out each assay conducted in Tables 4–7. The assay using polypeptide (II) as the solid phase antigen and the procedure described in Example 4A is referred to as the "ES" assay in those Tables. Sera that exhibited similar results in the assays performed are grouped together in the following tables to clarify the presentation of the data.

A. Table 4 shows results with normal sera.

TABLE 4

Assay of Normal Sera by ELISA Using Peptide (II)

| # of Samples | E8 Assay | ENI Assay | Abbott Assay | Diagnosis; Sample ID |
|---|---|---|---|---|
| 198 | – | 5-,194NT | 41-,156NT | Normal |
| 1 | – | – | + | Normal;749 |
| 1 | + | NT | NT | Normal;2846 |
| 200 | | | | |

Mean Absorbance of Normals = 0.016 for E8 assay
Standard Deviation (S.D.) from the mean = 0.017
Absorbance Cutoff Value at Mean + S.D. = 0.104
False Positive rate in 200 samples at 0.104 cutoff = 0.5% (1/200)
NT = Not Tested
Sample ID = Serum Sample Number As is shown in Table 4, subject sera not containing antibodies to HIV-1 generally do not react to peptide (II) in a standard ELISA. This permits calculation of an absorption cutoff value to distinguish between antibody-negative and antibody-positive sera. In the above assay of 200 normal sera, a cutoff value of 0.104 was selected. At this cutoff value the false positive rate is expected to be less than or equal to 0.5%.

B. To indicate the superior effectiveness for eliminating false positives by employing the peptide of formula (II) over the commercially available kits using viral lysate as target antigen, a number of sera from patients with two disorders unrelated to AIDS, namely naso-pharyngeal carcinoma and rheumatoid arthritis (RA), were tested by the E8 assay and commercial tests. The results are summarized in Table 5 below and indicate the increased specificity of the E8 assay. Many samples which gave false positive results with commercial tests were correctly identified as negative by the E8 assay.

TABLE 5

Test of Naso-Pharyngeal Carcinoma and Rheumatoid Arthritis Patients

| # of Samples | E8 Assay | ENI Assay | Abbott Assay | Diagnosis; Sample I.D. |
|---|---|---|---|---|
| 6 | (+) | NT | (+) | NPC/NON-AIDS |
| 17 | – | NT | (+) | NPC/NON-AIDS |
| 8 | – | NT | – | NPC/NON-AIDS |
| 1 | – | NT | NT | NPC/NON-AIDS |
| 1 | – | (+) | – | RA/NON-AIDS;920 |
| 7 | – | 2-,5NT | 3-,4NT | RA/NON-AIDS |
| 1 | – | – | (+) | RA/NON-AIDS;615 |

(+) = False Positives
NT = Not Tested
NPC = Naso-Pharyngeal Carcinoma
RA = Rheumatoid Arthritis C. To indicate the effectiveness of the E8 assay for detection of HIV-1 antibodies in AIDS/ARC patient sera compared to commercial kits, the ELISA kit described in Example 4-Procedure A was evaluated against a panel of sera derived from diagnosed AIDS and ARC patients. The results are summarized in Table 6 and show that the assay is equivalent to commercial kits for its ability to identify sera containing antibody to HIV-1.

TABLE 6

Assay of AIDS/ARC sera:

| # of Samples | E8 Assay | ENI Assay | Abbot Assay | Diagnosis; Sample I.D. |
|---|---|---|---|---|
| 67 | + | + | +(16NT) | AIDS |
| 2 | (–) | (–) | (–) | AIDS;533,3621 |
| 1 | (–) | + | + | AIDS;653 |
| 2 | + | + | (–) | AIDS;661,662 |
| 21 | + | + | + | ARC |
| 2 | (–) | (–) | (–) | ARC;512,529 |
| 95 | | | | |

(–) = False Negatives
ARC = Aids Related Complex
NT = Not Tested

D. The high rate of false positives characteristic of presently available kits using viral lysate as antigen is due in part to the presence of cellular antigens in the lysate that react with antibodies present in both AIDS and non-AIDS patient sera. Additionally, complex antigens such as those derived from a virus such as HIV-1 contain many epitopes and are more likely to react non-specifically with antibodies present in human sera.

The peptide (II) reduces the complexity of the antigen used to react with patient sera down to one or perhaps only a few epitopes. The chance of non-specific interaction with non-HIV-1 antibodies is therefore greatly reduced. Non-specific interactions, however, may still occur since some antibodies are "sticky" and can bind to the plastic support used in the assay, or to other proteins such as bovine serum albumin or goat sera used to block the plate after addition of the peptide.

Presented in Table 7 below are data relating to the assay of various patient sera. In addition to the usual assay with peptide (II) as described in Example 4-Procedure A, each serum was assayed against peptide (II) after mixing the serum sample with an effective blocking amount of the peptide (II). Also included in the Table are the results of assaying each sample with commercially available kits.

It is evident from these results that non-AIDS sera samples incorrectly identified as positive by either or both of the commercially available kits are correctly identified as negative using the E8 peptide competition assay. Furthermore, even samples incorrectly identified as positive by the E8 assay are correctly identified as negative by the E8 peptide competition assay. Significantly, the blocking or competition assay also serves as a confirmatory assay in assays of serum samples that do contain antibodies to HIV-1. The last seven samples assayed as shown in Table 7 are positive for antibody by both the E8 assay and commercially available assays (with the exception of two false negatives using the Abbott kit) and by the more tedious and time consuming Western blot assay. The reactivity of these sera with peptide (II) as solid phase antigen is effectively blocked by mixing each serum with peptide (II), indicating that the reactivity of antibody to peptide is peptide-specific, and that these last seven samples are true positives.

TABLE 7

Competition Assay Confirming Positive/Negative ELISA:

| | ELISA Value & Score with Peptide | | | | | |
|---|---|---|---|---|---|---|
| Samp. I.D. | Not Blocked | Blocked (Score) | Abbott Assay | ENI Assay | Western Assay | Diagnosis |
| 615 | 0.031 | 0.033(−) | − | − | − | RA |
| 3195 | 0.026 | 0.045(−) | − | +* | − | DP |
| 3196 | 0.028 | 0.039(−) | − | +* | − | DP |
| 3197 | 0.065 | 0.073(−) | − | +* | − | DP |
| 3376 | 0.104 | 0.105(−) | − | +* | − | UNK |
| 3362 | 0.740 | 0.727(−) | − | +* | − | UNK |
| 912 | 0.055 | 0.065(−) | +* | NT | − | NPC |
| 918 | 0.100 | 0.092(−) | +* | NT | − | NPC |
| 922 | 0.127 | 0.103(−) | +* | NT | NT | NPC |
| 923 | 0.114 | 0.080(−) | +* | NT | NT | NPC |
| 3644 | 0.336 | 0.380(−) | +* | +* | − | UNK |
| 3406 | 1.400 | 1.390(−) | +* | +* | − | DP |
| 3461 | 1.426 | 1.137(−) | +* | +* | − | DP |
| 3532 | 1.770 | 0.080(+) | + | + | + | UNK |
| 3469 | 0.300 | 0.030(+) | + | + | + | UNK |
| 3431 | 0.507 | 0.087(+) | NT | + | + | UNK |
| 644 | 0.160 | 0.024(+) | NT | + | + | AIDS |
| 659 | 0.510 | 0.042(+) | + | + | + | AIDS |
| 661 | 0.500 | 0.031(+) | −** | + | + | AIDS |
| 662 | 0.160 | 0.030(+) | −** | + | + | AIDS |

* = False Positive
** = Flase Negative
DP = Dialysis Patient, Non-Aids
NPC = Naso-Pharyngeal Carcinoma, Non-Aids
UNK = Unknown
RA = Rheumatoid Arthritis, Non-Aids
(−) and − = HIV-1 Antibody Negative
(=) and + = HIV-1 Antibody Positive 6. Comparison of HIV-1 Peptides (I)-(XV) and (C-I)-(C-III) by ELISA Elisa kits as described in Example 4-Procedure A were made with peptides (I) through (XV) as well as (C-I) through (C-VIII). The ELISA kits were each evaluated against a ten sample panel of sera comprising clinically positive samples, i.e., samples that evidenced the presence of HIV-1 infection as determined by commercial assays and Western blot assay. The results of these assays are shown in Table 8 below.

A peptide assay is considered positive if the absorbance (optical density) level of the ELISA assay was more than twice the background level as determined by averaging the absorbance of two normal sera. The mean value reported represents the mean optical density value of the ELISA as calculated after the background value was subtracted. The index reported is a weighted activity of a given peptide relative to the activity of the peptide of formula (II). The index is weighted in favor of the ability of a particular peptide assay to correctly report a positive value as distinguished from the level of the background normal response. The formula for deriving the index is as follows:

$$\frac{(\%\ \text{Positive})^3 \times \text{MEAN}}{(\%\ \text{Positive}_{II})^3 \times \text{MEAN}_{II}} = \text{Index}$$

wherein: % Positive is % Positive for the given peptide assay;

MEAN is MEAN for the given peptide assay;

% $\text{Positive}_{II}$ is % Positive for peptide assay having the formula (II); and % $\text{MEAN}_{II}$ is MEAN for the peptide assay having the formula (II).

As can be seen from Table 8, assays made using peptides having the formulas (I) through (V), all provide positive results of at least 50% or greater and in each case manifest an index of at least 0.1. On the other hand, each of the comparative segments, although representing closely adjacent or overlapping or partially overlapping segments from the HIV-1 envelope, fail to exhibit such positive results or such high index. These data also show that use of a mixture of polypeptides (III) and (IV) provides an improved result as to mean and index values than does polypeptide (V) whose sequence contains the combination of the sequences of (III) and (IV).

TABLE 8

| PEPTIDE FORMULA | SEQUENCE | % POSITIVE | MEAN | INDEX |
|---|---|---|---|---|
| (II) | S,22 IWGCSGKLICTTAVP | 80 | 1.67 + 0.82 | 1.00 |
| (C-V) | QLTVWGIKQLQARIL | 0 | — | 0 |
| (C-VI) | GIKQLQARILAVERY | 20 | 0.45 + 0.06 | 0.01 |
| (C-I) | QLQARILAVERY | 0 | — | 0 |
| (C-IX) | QARILAVERYLKDQQ | 0 | — | 0 |
| (XV) | RILAVERYLKDQQLLGI-WGCS | 90 | 2.01 + 1.40 | 1.56 |
| (C-II) | AVERYLKDQQLLG | 10 | 0.04 — | >0.01 |
| (C-VII) | AVERYLKDQQLLGIW | 60 | 1.18 + 0.68 | 0.35 |
| (IV) | AVERYLKDQQLLGIWGCS-GKLI | 100 | 2.23 + 0.68 | 2.26 |
| (XII) | AVERYLKDQQLLGIWGCS-GKLIC | 100 | 1.95 + 0.27 | 2.11 |
| (C-III) | LKDQQLLGIWGCS | 30 | 0.28 + 0.06 | 0.02 |

TABLE 8-continued

| PEPTIDE FORMULA | SEQUENCE | % POSITIVE | MEAN | INDEX |
|---|---|---|---|---|
| (XIV) | LKDQQLLGIWGCSGK | 90 | 1.69 + 0.65 | 1.43 |
| (VI) | LKDQQLLGIWGCSGKLI | 100 | 1.19 + 0.85 | 1.65 |
| (VII) | LLGIWGCSGKLIC | 50 | 0.22 + 0.05 | 0.09 |
| (XI) | LLGIWGCSGKLICTT | 80 | 1.53 + 0.77 | 0.96 |
| (C-IV) | IWGCSGKLI | 20 | 0.17 + 0.00 | 0.01 |
| (I) | CSGKLIC | 60 | 0.34 + 0.11 | 0.19 |
| (VIII) | QQLLGIWGCSGKLICT-TAVPWNAS | 90 | 0.51 + 0.25 | 0.79 |
| (IX) | IWGCSGKLICTTAVPWN | 70 | 0.86 + 0.45 | 0.48 |
| (III) | IWGCSGKLICTTAVPW-NAS | 100 | 2.20 + 0.86 | 2.24 |
| (XIII) | GCSGKLICTTAVPWN | 100 | 2.14 + 0.58 | 2.21 |
| (X) | CSGKLICTTAVPWNAS | 100 | 1.74 + 1.01 | 1.99 |
| (XI) | SGKLICTTAVPWNAS | 50 | 0.86 + 0.63 | 0.17 |
| (C-VIII) | LICTTAVPWNASWSN | 0 | — | 0 |
| (V) | AVERYLKDQQLLGIWGCS-GKLICTTAVPWNAS | 100 | 1.53 + 0.66 | 1.89 |
| (III) & (IV) | AVERYLKDQQLLGIWGCS-GKLI + IWGCSGKLICTTAVPW-NAS | 100 | >3.0 — | 2.62 |

7. Comparison of ELISAs Using HIV-1 Peptides (III) and (IV)

Additional AIDS/ARC patient sera were assayed with ELISA assays employing the two highly reactive peptides of formulas (III) and (IV) (Example IV-Procedure 1). The reactivity, expressed as absorbance values, of some of these sera is shown in Table 9.

TABLE 9

| | | PEPTIDE FORMULA | |
|---|---|---|---|
| | SERUM SAMPLE | (III) | (IV) |
| A. | 3362 | 0.503 | 0.151 |
| | 3412 | >2.00 | 0.540 |
| | 3693 | 0.559 | 0.120 |
| | 3722 | 0.620 | 0.193 |
| | 0649 | 1.756 | 0.379 |
| B | 3555 | 0.428 | >2.00 |
| | 3575 | 0.350 | 1.773 |
| | 3744 | 0.311 | 1.326 |
| | 3790 | 0.224 | 1.765 |
| | 0509 | 0.403 | 2.000 |
| | 0653 | 0.111 | 0.999 |
| | 0662 | 0.301 | 1.392 |
| C. | 3416 | 1.914 | >2.00 |
| | 3456 | 1.670 | 1.780 |
| | 3666 | >2.00 | >2.00 |
| | 3414 | 1.453 | 1.057 |
| | 3411 | >2.00 | >2.00 |
| | 3413 | >2.00 | >2.00 |

Most sera assayed reacted very well with both peptides, much as is seen with samples in Table 9, group C. Occasionally, however, some samples were far more reactive with one peptide than the other, as shown in Table 9, groups A and B. These data indicate that there may be more than one epitope (e.g., a linear and a conformational epitope or two linear epitopes) in this thirty-two amino acid region that is commonly recognized by patients that have been exposed to HIV-1. High performance liquid chromatography (HPLC) analysis of peptides of formulas (III) and (IV) in solution indicate that formula (III) peptides exist largely as cyclic monomers, while formula (IV) peptides are mostly in dimer form. The structural characteristcs imparted to these two peptides by disulfide bonding may be related to both antigen presentation and the creation of a conformation epitope.

The differential reactivity of polypeptides (III) and (IV) was further examined by comparing the absorbance values obtained for each peptide in ELISAs performed according to Example 4B using peptide (III), peptide (IV) or a combination of (III) and (IV) as solid phase antigen. The absorbance values obtained for each of 37 sera in the peptide (III) based ELISA were divided by those obtained in the peptide (IV) based ELISA. The resulting absorbance value ratios are shown in ranked order in Table 10.

From Table 10 it can be seen that 30 out of the 37 sera examined demonstrated a greater immunoreactivity for peptide (III) than peptide (IV).

TABLE 10

| Comparison of Polypeptides (III) and (IV) | | | | |
|---|---|---|---|---|
| Serum No. | (III) | (IV) | Ratio (III):(IV) | (III) + (IV) |
| 4099 | 2.000 | 0.018 | 111.11 | 2.000 |
| 4074 | 0.980 | 0.019 | 51.58 | 1.260 |
| 4084 | 2.000 | 0.039 | 51.28 | 1.834 |
| 0641 | 0.641 | 0.014 | 45.79 | 0.834 |
| 4109 | 2.000 | 0.088 | 22.73 | 2.000 |
| 4100 | 2.000 | 0.105 | 19.05 | 1.930 |
| 3228 | 1.682 | 0.125 | 13.46 | 1.538 |
| 3868 | 0.200 | 0.022 | 9.09 | 0.572 |
| 4062 | 0.187 | 0.022 | 8.50 | 0.422 |
| 4089 | 0.756 | 0.108 | 7.00 | 1.130 |
| 3869 | 0.548 | 0.134 | 4.09 | 1.019 |
| 4008 | 0.664 | 0.215 | 3.09 | 1.246 |
| 4067 | 1.806 | 0.644 | 2.80 | 1.780 |
| 4068 | 1.773 | 0.649 | 2.73 | 1.898 |
| 4007 | 1.866 | 0.776 | 2.40 | 1.730 |
| 4086 | 1.503 | 0.644 | 2.33 | 1.473 |
| 3980 | 0.280 | 0.131 | 2.14 | 0.560 |
| 4082 | 1.518 | 0.786 | 1.93 | 1.781 |
| 3544 | 0.322 | 0.167 | 1.93 | 0.385 |
| 4006 | 0.214 | 0.120 | 1.78 | 0.340 |
| 4071 | 0.810 | 0.504 | 1.61 | 1.164 |
| 4117 | 2.000 | 1.262 | 1.58 | 1.955 |
| 4078 | 2.000 | 1.318 | 1.52 | 2.000 |
| 4095 | 2.000 | 1.396 | 1.43 | 2.000 |
| 3281 | 0.804 | 0.569 | 1.41 | 1.544 |

TABLE 10-continued

| Comparison of Polypeptides (III) and (IV) | | | | |
|---|---|---|---|---|
| Serum No. | (III) | (IV) | Ratio (III):(IV) | (III) + (IV) |
| 4111 | 2.000 | 1.587 | 1.26 | 2.000 |
| 4092 | 0.552 | 0.462 | 1.19 | 1.764 |
| 4010 | 2.000 | 1.832 | 1.09 | 2.000 |
| 4063 | 0.642 | 0.597 | 1.08 | 0.848 |
| 3226 | 2.000 | 1.897 | 1.05 | 2.000 |
| 4083 | 2.000 | 2.000 | 1.00 | 2.000 |
| 4110 | 1.964 | 2.000 | 0.98 | 2.000 |
| 3455 | 0.239 | 0.244 | 0.98 | 0.196 |
| 3785 | 0.170 | 0.352 | 0.48 | 0.493 |
| 4077 | 0.400 | 1.040 | 0.38 | 1.290 |
| 4115 | 0.042 | 0.150 | 0.28 | 0.271 |
| 3983 | 0.070 | 1.767 | 0.04 | 1.988 |

8. HIV-1 Peptide Competitive Inhibition Studies

Further evidence that more than one epitope is present in formula (III) and (IV) peptides can be deduced from absorbance values obtained from competition studies, the results of an example of which are shown in Table 11. In this study, admixed formula (III) and (IV) peptides were applied to a microtiter plate as the immobilized, solid phase antigen and an ELISA assay (Example 4A) was performed under five different conditions:without competition, or competition with excess formula (III) peptide, formula (IV) peptide, an admixture of both peptides [(III)+(IV)], or with a heterologous peptide. The competition was performed by adding the appropriate peptide(s) to the diluted serum just before adding the serum sample to the microtiter well.

TABLE 11

| | | COMPETING PEPTIDE FORMULA | | | |
|---|---|---|---|---|---|
| SAMPLE | UNBLOCKED | (III) | (IV) | (III) + (IV) | HETEROLOGOUS |
| 3412 | 1.450 | 0.113 | 1.182 | 0.059 | 1.348 |
| 3413 | >2.00 | 0.381 | 2.032 | 0.068 | 2.026 |
| 3416 | >2.00 | 1.811 | 1.055 | 0.197 | 2.041 |
| 3544 | 1.810 | 0.876 | 0.137 | 0.048 | 1.750 |
| 3575 | 1.267 | 0.982 | 0.105 | 0.036 | 1.304 |
| 3693 | 0.340 | 0.103 | 0.217 | 0.065 | 0.293 |
| 3790 | 1.558 | 1.320 | 0.635 | 0.134 | 1.349 |

Under these conditions it is very clear that some samples react very well with each or both of peptides (III) and (IV). For example, sample 3416 reacted well with an admixture of both peptides, since competition with the formula (III) peptide alone gave an optical density (OD) of>1.8, competition with the formula IV peptide yielded an OD of 1.055 and, in the presence of both competing peptides, the OD went down essentially to background levels. Other serum samples such as 3412 reacted much more strongly with one peptide than the other; in this case, the OD was reduced from>1.4 down to 0.113 when blocked with formula (III) peptide, and remained>1 when competed with formula (IV) peptide. However, there is clearly some reactivity with formula (IV) peptide because, in the presence of both peptides, immunoreactivity is completely abolished (0.059). Still further, admixture of peptides (III) and (IV) as competing peptides always provided a better result than did the use of either peptide alone.

Another competition study with the formula (I) peptide on the plate as solid phase antigen and using the procedure of Example 4A, showed that formula (IV) peptide did not effectively compete with formula (I) peptide although the formula (III) peptide competed very effectively. See Table 12 below.

TABLE 12

| | | COMPETING PEPTIDE FORMULA | | | |
|---|---|---|---|---|---|
| SAMPLE | UNBLOCKED | (I) | (III) | (IV) | HETEROLOGOUS |
| 013 | 1.177 | 0.038 | 0.046 | 0.770 | 0.865 |
| 014 | 0.383 | 0.050 | 0.067 | 0.273 | 0.324 |

Thus, it appears from these analysis that an epitope present in formula (III) peptide is also present on formula (I) peptide, and that this epitope is substantially different from those present in formula (IV) peptide. Furthermore, based on this same sample, virtually all sera reacted with the epitopes presented on the formula (III) and (IV) peptides, although in many cases, more strongly with one peptide than with the other.

9. ELISA Using a Combination of HIV-1 Peptides (III) and (IV)

Using a combination of one microgram of formula (III) and 0.5 ug of formula (IV) peptides per well as the solid phase antigen in an ELISA assay (Example 4B), the specificity and sensitivity of this assay was equal or superior to any of the commercially available vital lysate antibody detection kits tested.

Table 13 presents ELISA results obtained using patient sera, normal sera, and sera from miscellaneous disease groups that include rheumatoid arthritis, naso-pharyngeal carcinoma, Epstein-Barr virus infection, cytomegalovirus infection, gram negative sepsis, toxoplasma gondii, systemic lupous erythematosus, and herpes virus infections.

TABLE 13

| SAMPLE GROUP | NUMBER OF SERA | ENI POS | (III) + (IV) POS | ENI NEG | (III) + (IV) NEG |
|---|---|---|---|---|---|
| AIDS + ARC | 458(243)* | 449 | 450 | 9 | 8 |
| SYMPTOMATIC PLS | 320(146) | 239 | 242 | 81 | 78 |
| ASYMPTOMATIC/ HIGH RISK IMMUNE ABNORMALITIES | 135(87) | 38 | 39 | 97 | 96 |
| ASYMPTOMATIC/ HIGH RISK IMMUNE NORMAL | 134(69) | 10 | 10 | 124 | 124 |
| NORMAL/NON-AIDS | 728(728) | 12 | 4 | 716 | 724 |
| MISCELLANEOUS DISEASE GROUPS/NON-AIDS | 387(387) | 10 | 7 | 377 | 380 |
| TOTAL NON-AIDS | 1115 | 22 | 11 | 1093 | 1104 |

*Numbers in parentheses indicate number of patients

When bona fide normal sera were assayed for reactivity in the (III)+(IV) assay and in the assay marketed by Electronucleonics, Incorporated (ENI), the (III)+(IV) peptide assay had a significantly lower false positive rate. As the data of Table 13 show, the false positive rate for ENI was 1.65% (12/728), whereas the (III)+(IV) peptide assay had a false positive rate of only 0.55% (4/728). When the false positive rate in the Miscellaneous Disease Group is examined, the peptide assay had a slightly lower false positive rate than did the ENI assay, 1.81% vs. 2.58% (7/387 vs. 10/387).

10. Synthesis of STLV-III-related Polypeptides

Synthesis of polypeptides p80 and p81 was accomplished using substantially the same classical Merrifield technique as described earlier. For peptide p80, Boc-cysteine resin with substitution of 0.71 mMole/gram, prepared as in Example 2, was used. For peptide p81, Boc-serine resin with substitution of 0.67 mMole/gram, prepared as in Example 2, was used.

A. For polypeptide p80, the amino acid residue sequence AIEKYLEDQAQLNAWCAFRQVC was synthesized using the following Boc-L-amino acids in twelve molar equivalents (meq) excess:

| Amino Acid | Solvent |
|---|---|
| Boc-Val | $CH_2Cl_2$ |
| Boc-Gln/Hobt | DMF |
| Boc-(Tosyl)-Arg | 10% DMF/$CH_2Cl_2$ |
| Boc-Phe | $CH_2Cl$ |
| Boc-Ala | $CH_2Cl_2$ |
| Boc-(MeOBzl)-Cys | $CH_2Cl_2$ |
| Boc-Trp | 10% DMF/$CH_2Cl_2$ |
| Boc-Ala | $CH_2Cl_2$ |
| Boc-Asn/Hobt | DMF |
| Boc-Leu | 10% DMF/$CH_2Cl_2$ |
| Boc-Gln/Hobt | DMF |
| Boc-Ala | $CH_2Cl_2$ |
| Boc-Gln/Hobt | DMF |
| Boc-(Bzl)-Asp | $CH_2Cl_2$ |
| Boc-(Bxl)-Blu | $CH_2Cl_2$ |
| Boc-Leu | 10% DMF/$CH_2Cl_2$ |
| Boc-(Br-Z)-Typ | $CH_2Cl_2$ |
| Boc-(Cl-Z)-Lys | $CH_2Cl_2$ |
| Boc-(Bzl)-Glu | $CH_2Cl_2$ |
| Boc-Ile | $CH_2Cl_2$ |
| Boc-Ala | $CH_2Cl_2$ |

B. For polypeptide p81, the amino acid residue sequence AWCAFRQVCHTTVPWPNAS was synthesized using the following Boc-L-amino acids in twelve meq excess:

| Amino Acid | Solvent |
|---|---|
| Boc-Ala | $CH_2Cl_2$ |
| Boc-Asn/Hobt | DMF |
| Boc-Pro | $CH_2Cl_2$ |
| Boc-Trp | 10% DMF/$CH_2Cl_2$ |
| Boc-Pro | $CH_2Cl_2$ |
| Boc-Val | $CH_2Cl_2$ |
| Boc-(O-Bzl)-Thr | $CH_2Cl_2$ |
| Boc-(O-Bzl)-Thr | $CH_2Cl_2$ |
| Boc-(Z-Carbobenzoxy)-His | $CH_2Cl_2$ |
| Boc-(MeOBzl)-Cys | $CH_2Cl_2$ |
| Boc-Val | $CH_2Cl_2$ |
| Boc-Gln/Hobt | DMF |
| Boc-(Tosyl)-Arg | 10% DMF/$CH_2Cl_2$ |
| Boc-Phe | $CH_2Cl_2$ |
| Boc-Ala | $CH_2Cl_2$ |
| Boc-(MeOBzl)-Cys | $CH_2Cl_2$ |
| Boc-Trp | 10% DMF/$CH_2Cl_2$ |
| Boc-Ala | $CH_2Cl_2$ |

Polypeptides were individually cleaved from the respective resins, extracted with acetic acid, run through a Fractogel desalting column and were analyzed as in Example 1.

11. Evaluation of STLV-III Polypeptides P80 and P81, Alone and in Combination, by ELISA Preliminary studies using two sera containing high titers of antibodies against HIV-2 were performed by ELISA using each of p80 and p81 alone and in combination. One hundred microliters (ul) of 0.01M $NaHCO_3$, pH 9.6, containing 1 microgram (ug) of either p80 or p81 or a combination (admixture) of 1 ug of p80 and 1 ug of p81 were admixed into the wells of Immunolon II microtiter plates (Dynatech, Alexandria, Va.). The plates were then maintained for about 16 hours at 4 degrees C. to permit the polypeptides to adsorb onto (coat) the walls of the wells. After removing the polypeptide coating solution by shaking, 300 ul of PBS containing 1% bovine serum albumin (BSA), 5 mM benzamidine, 10 kilounits Aprotinin, 10 ug/ml Trypsin Inhibitor, 10 mM EACA, 0.5 mM PMSF, 2 mM EDTA and 10% glycerol were admixed into each well to block excess protein binding sites.

The wells were maintained 90 minutes at 37 degrees C., the blocking solution was removed by shaking, and the wells were dried by maintaining them for 1 hour at 37 degrees C., thus forming a diagnostic system of the present invention, i.e., a STLV-III-related polypeptide-containing solid support (polypeptide-coated well).

Two hundred ul of each serum diluted 1:10 in TBS were admixed into a polypeptide-coated well. The resulting solid-liquid phase immunoreaction admixture was maintained at 37 degrees C. for 30 minutes to permit formation of polypeptide-containing immunoreaction products. The wells were then rinsed 5 times with PBS containing 0.05% Tween20.

Two hundred ul of a horseradish peroxidase-labeled mouse monoclonal anti-human IgG antibody (Ortho Diagnostic Systems, Inc., Raritan, N.J.), diluted 1:3500 in PBS containing 50% fetal calf serum, 1% horse serum and 0.5% Tween20, were then admixed into each well. The resulting labeling-reaction admixture was maintained for 30 minutes at 37 degrees C. to permit formation of polypeptide-containing labeled complexes. The wells were then rinsed 5 times with PBS-0.05% Tween20 to remove non-reacted labeled-antibody.

Two hundred ul of OPD substrate were then admixed into each well to form a developing-reaction admixture. After maintaining the developing-reaction admixture for 30 minutes at about 20 degrees C., 50 ul of 4N $H_2SO_4$ were admixed into each well to stop the developing-reaction, and the resulting solutions were assayed for absorbance at 490 nm using a microtiter plate reader.

The results of the these studies indicated that both p80 and p81 are capable of immunoreacting with antibodies induced by HIV-2. Polypeptide p80 produced absorbance values of greater than 1.1 with both sera, whereas p81 produced values of about 0.4. When the ELISAs were performed using an admixture of p80 and p81, absorbance values comparable to those obtained with p81 alone were seen.

12. HIV-1 and STLV-III Polypeptide Specificity Studies

Three groups of sera were used to evaluate the ability to the HIV-1 and STLV-III polypeptides to distinguish between antibodies induced by HIV-1 and HIV-2 infections. The first group consisted of 20 sera obtained from HIV-2 isolate antibody positive West African patients collected while they were attending an outward clinic in Bissau, Guinea-Bissau, for examinations related to suspected tuberculosis. All of these sera immunoreacted with HIV-2 by ELISA using disrupted virons (viral lysate) as antigen. These sera also contained antibodies that reacted with the TMP (gp36) of HIV-2 in a Western blot assay, but demonstrated no reactivity with the TMP (gp41) of HIV-1.

The second group included sera from 20 HIV-1 antibody positive asymptomatic Swedish subjects (homosexual men, intravenous drug abusers or hemophiliacs) reacting in the Western blot assay with the TMP (gp41) and other antigens of HIV-1, but not with the TMP (gp36) of HIV-2.

The third group consisted of 20 sera from Swedish blood donors negative for HIV-1 and HIV-2 antibodies when assayed using commercially abailable diagnostic systems obtained from Organon, Teknika, N. V., Tunhout, Belgium, and Wellcome Reagents, Ltd., London, U.K. and the HTLV-IV viral lysate ELISA.

Solid supports comprising a combination of HIV-1 polypeptides (III) and (IV) affixed to microtiter plate wells were prepared as described in Example 11 using 200 ul of 0.1M $NaHCO_3$, pH 9.6, containing 5 ug/ml of each polypeptide to coat the wells. Also prepared according to Example 11 were a different set of solid supports comprising STLV-III polypeptide p80 affixed to microtiter plate wells. All three groups of the above described sera were then assayed using both the (III)+(IV) polypeptide combination-containing (HIV-1 specific) and p80-containing (HIV-2 specific) solid supports according to the ELISA procedure of Example 11.

Figure 3B:
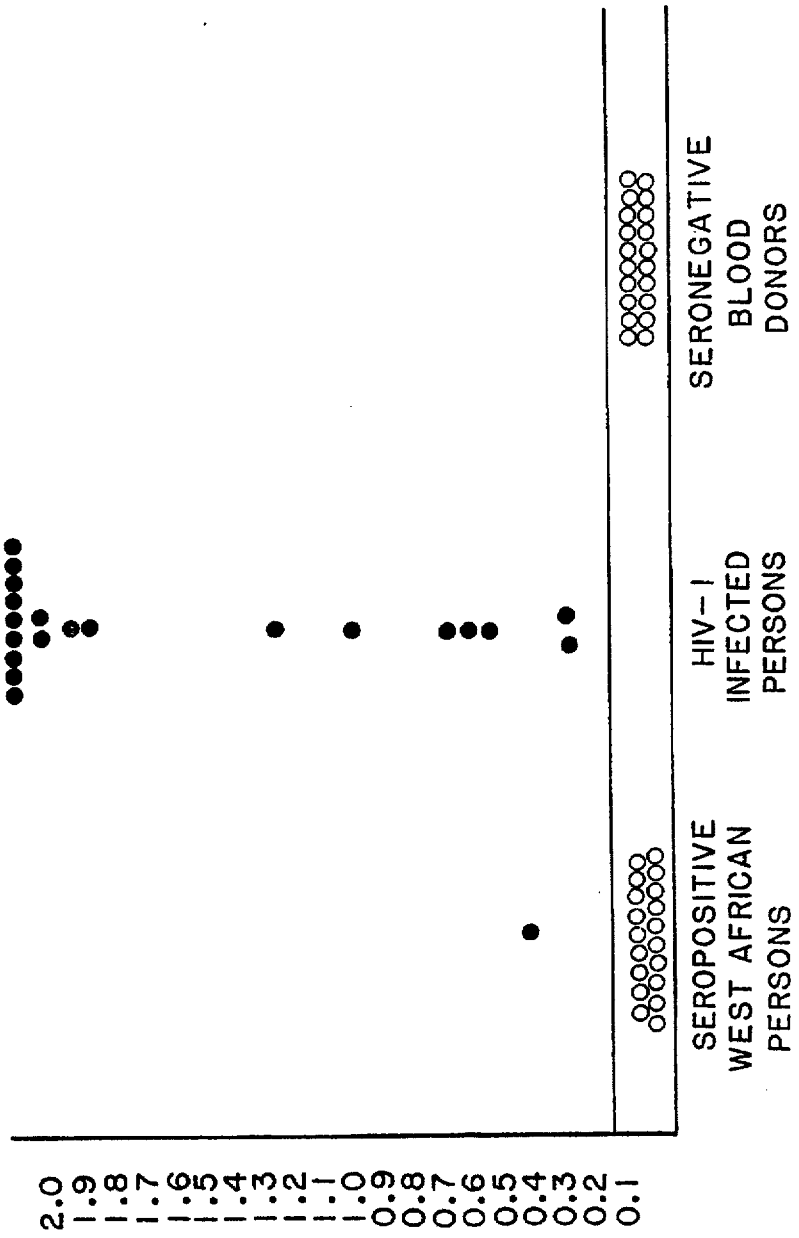

The ELISA results of all three groups of sera are illustrated in FIG. 3. The 20 sera containing antibodies to HIV-2 but not to HIV-1 TMP gp41 gave pronounced reactions with STLV-III-related polypeptide p80 but, except for one serum, produced no substantial immunoreaction with the combination of HIV-1-related polypeptides (III) and (IV).

In contradistinction, the 20 sera with antibodies against HIV-1 reacted with the solid supports containing polypeptides (III) and (IV) but, again with one exception, produced no substantial immunoreaction with the solid supports containing only p80. The negative control sera did not produce any substantial immunoreaction with either the HIV-1- or STLV-III-specific solid supports.

From subsequent analysis of the two sera producing immunoreaction with both HIV-1- and STLV-III-specific solid supports it is believed that the individuals from whom those sera were obtained had been exposed to both the HIV-1 and HIV-2 viruses.

Because polypeptides (III) and (IV) were found to be differentially reactive, (Example 7), polypeptides p80 and p81 were similarly compared. The absorbance values obtained for each of 24 sera in a peptide p80 based ELISA were divided by those obtained in a peptide p81 based ELISA. The resulting absorbance value ratios are shown in ranked order in Table 14.

From Table 14 it can be seen that 19 out of the 24 sera examined demonstrated a greater immunoreactivity for p80 than for p81.

Thus, the present invention provides an assay system and method for distinguishing between exposure to HIV-1 versus exposure to HIV-2 as well as exposure to either.

TABLE 14

Comparison of Peptides p80 and p81

| Serum No. | p80 | p81 | Ratio p80:p81 |
|---|---|---|---|
| 6602 | 0.516 | 0.001 | 516.000 |
| 6698 | 2.000 | 0.022 | 90.910 |
| 5740 | 2.000 | 0.043 | 46.510 |
| 6877 | 0.248 | 0.008 | 31.000 |
| 6650 | 0.700 | 0.034 | 20.590 |
| 3616 | 0.686 | 0.047 | 14.600 |
| 3942 | 0.588 | 0.051 | 11.530 |
| 6674 | 2.000 | 0.258 | 7.752 |
| 3541 | 0.181 | 0.025 | 7.240 |
| 3743 | 0.257 | 0.040 | 6.425 |
| 6665 | 0.254 | 0.053 | 4.792 |
| 6604 | 1.808 | 0.400 | 4.520 |
| 6661 | 0.647 | 0.160 | 4.044 |
| 6603 | 1.152 | 0.421 | 2.736 |
| 3923 | 0.180 | 0.067 | 2.687 |
| 6601 | 0.353 | 0.138 | 2.558 |
| 5182 | 0.162 | 0.102 | 1.588 |
| 6600 | 0.359 | 0.306 | 1.173 |
| 5160 | 0.251 | 0.236 | 1.064 |
| 5727 | 0.504 | 0.563 | 0.895 |
| 6599 | 0.206 | 0.232 | 0.888 |

TABLE 14-continued

Comparison of Peptides p80 and p81

| Serum No. | p80 | p81 | Ratio p80:p81 |
|---|---|---|---|
| 6683 | 0.387 | 0.489 | 0.791 |
| 6631 | 0.153 | 0.285 | 0.537 |
| 6598 | 0.072 | 0.205 | 0.351 |

The foregoing specification, including the specific embodiments and examples, is intended to be illustrative of the present invention and is not to be taken as limiting. Numerous other variations and modifications can be effected without department from the true spirit and scope of the present invention.

What is claimed is:

1. A polypeptide consisting of the following amino acid sequence, AIEKYLEDQAQLNAWGCAFRQVCHTTVPWPNAS, or a polypeptide containing no more than 33 amino acid residues and differing from this sequence by no more than ten percent of the amino acid sequence, wherein said polypeptide contains the sequence —CAFRQVC—, displays immunological cross-reactivity with HIV-2 transmembrane envelope glycoprotein-specific antibodies, and fails to display immunological cross-reactivity with HIV-1 transmembrane envelope glycoprotein-specific antibodies.

2. A polypeptide consisting of one of the following amino acid sequences, AIEKYLEDQAQLNAWGCAFRQVC, AVEKYLKDQAQLNAWGCAFRQVC, AIEKYLKDQAQLNSWGCAFRQVC, and AIEKYLEDQAQLNAWCAFRQVC, or a polypeptide differing from one of these sequences by no more than ten percent of the amino acid sequence, wherein said polypeptide contains the sequence —CAFRQVC—, displays immunological cross-reactivity with HIV-2 transmembrane envelope glycoprotein-specific antibodies, and fails to display immunological cross-reactivity with HIV-1 transmembrane envelope glycoprotein-specific antibodies.

3. A polypeptide consisting of the following amino acid sequence AIEKYLEDQAQLNAWCAFRQVC.

4. A polypeptide consisting of the following amino acid sequence AIEKYLEDQAQLNAWGCAFRQVC.

5. A polypeptide consisting of the following amino acid sequence AVEKYLKDQAQLNAWGCAFRQVC.

6. A polypeptide consisting of the following amino acid sequence AIEKYLKDQAQLNSWGCAFRQVC.

7. A polypeptide consisting of one of the following amino acid sequences, AWCAFRQVCHTTVPWPNAS, SWGCAFRQVCHTSVPWVNDT, AWGCAFRQVCHTTVPWPNAS, and AWGCAFRQVCHITVPWPNAS, or a polypeptide differing from one of these sequences by no more than ten percent of the amino acid sequence, wherein said polypeptide contains the sequence —CAFRQVC—, displays immunological cross-reactivity with HIV-2 transmembrane envelope glycoprotein-specific antibodies, and fails to display immunological cross-reactivity with HIV-1 transmembrane envelope glycoprotein-specific antibodies.

8. A polypeptide consisting of the following amino acid sequence AWCAFRQVCHTTVPWPNAS.

9. A polypeptide consisting of the following amino acid sequence SWGCAFRQVCHTSVPWVNDT.

10. A polypeptide consisting of the following amino acid sequence AWGCAFRQVCHTTVPWPNAS.

11. A polypeptide consisting of the following amino acid sequence AWGCAFRQVCHITVPWPNAS.

12. A method of assaying for the presence of anti-HIV-2 antibodies in a body fluid sample comprising the following steps:

a) admixing a body fluid sample with a polypeptide containing no more than 33 amino acid residues, said polypeptide consisting of one of the following amino acid sequences, AIEKYLEDQAQLNAWGCAFRQVCHITVPWPNAS, AIEKYLEDQAQLNAWCAFRQVC, AVEKYLKDQAQLNAWGCAFRQVC, AIEKYLKDQAQLNSWGCAFRQVC, AIEKYLEDQAQLNAWGCAFRQVC, AWCAFRQVCHTTVPWPNAS, SWGCAFRQVCHTSVPWVNDT, AWGCAFRQVCHTTVPWPNAS, and AWGCAFRQVCHITVPWPNAS, or a polypeptide differing from one of these sequences by no more than ten percent of the amino acid sequence, wherein said polypeptide contains the sequence —CAFRQVC—, displays immunological cross-reactivity with HIV- 2 transmembrane envelope glycoprotein-specific antibodies, and fails to display immunological cross-reactivity with HIV-1 transmembrane envelope glycoprotein-specific antibodies;

b) allowing the polypeptide and anti-HIV-2 antibodies present in the body fluid sample to form a polypeptide-containing immunoreaction product; and, c) detecting the presence of anti-HIV-2 antibodies in said immunoreaction product.

13. The method according to claim 12 wherein said polypeptide-containing immunoreaction product is detected according to step (c) by the following additional steps:

d) admixing the polypeptide-containing immunoreaction product with a labeled human immunoglobulin-specific binding agent under conditions that permit the labeled agent to bind to anti-HIV-2 antibodies present in the product thereby forming a labeled polypeptide-containing immunoreaction product;

e) detecting the formation of said labeled polypeptide-containing immunoreaction product.

14. A diagnostic kit for the detection of anti-HIV-2 antibodies in a body fluid sample comprising a package containing a polypeptide containing no more than 33 amino acid residues and consisting of one of the following amino acid sequences, AIEKYLEDQAQLNAWGCAFRQVCHTTVPWPNAS, AIEKYLEDQAQLNAWCAFRQVC, AVEKYLKDQAQLNAWGCAFRQVC, AIEKYLKDQAQLNSWGCAFRQVC, AIEKYLEDQAQLNAWGCAFRQVC, AWCAFRQVCHTTVPWPNAS, SWGCAFRQVCHTSVPWVNT, AWGCAFRQVCHTTVPWPNAS, and AWGCAFRQVCHITVPWPNAS, or a polypeptide that differs from this sequence by no more than ten percent of the amino acid sequence, wherein said polypeptide has the sequence —CAFRQVC—, displays immunological cross-reactivity with HIV-2 transmembrane envelope glycoprotein-specific antibodies, and fails to display immunological cross-reactivity with HIV-1 transmembrane envelope glycoprotein-specific antibodies.

15. The diagnostic kit according to claim 14 which further includes, in a separate package, a labeled reagent for the detection of polypeptide-containing immunoreaction products.

* * * * *